(12) United States Patent
Masuda et al.

(10) Patent No.: US 10,428,112 B2
(45) Date of Patent: Oct. 1, 2019

(54) MULTIPLEXED SAME TYPE-ANTIGENIC PEPTIDE

(71) Applicants: RIKEN, Wako-shi, Saitama (JP); ANIMAL ALLERGY CLINICAL LABORATORIES INC., Sagamihara-shi, Kanagawa (JP); NIPPON ZENYAKU KOGYO CO., LTD., Koriyama-shi, Fukushima (JP)

(72) Inventors: Kenichi Masuda, Sagamihara (JP); Yasuyuki Ishii, Wako (JP); Toshihiro Tsukui, Koriyama (JP)

(73) Assignees: RIKEN, Wako-shi, Saitama (JP); Animal Allergy Clinical Laboratories Inc., Sagamihara-shi, Kanagawa (JP); Nippon Zenyaku Kogyo Co., Ltd., Koriyama-shi, Fukushima (JP)

( * ) Notice: Subject to any disclaimer, the term of this patent is extended or adjusted under 35 U.S.C. 154(b) by 172 days.

(21) Appl. No.: 15/317,693

(22) PCT Filed: Jun. 11, 2015

(86) PCT No.: PCT/JP2015/066865
§ 371 (c)(1),
(2) Date: Jan. 19, 2017

(87) PCT Pub. No.: WO2015/190555
PCT Pub. Date: Dec. 17, 2015

(65) Prior Publication Data
US 2017/0158738 A1    Jun. 8, 2017

(30) Foreign Application Priority Data

Jun. 11, 2014 (JP) .................. 2014-120999

(51) Int. Cl.
*A61K 39/00* (2006.01)
*C07K 7/08* (2006.01)
(Continued)

(52) U.S. Cl.
CPC ............... *C07K 7/08* (2013.01); *A61K 39/00* (2013.01); *A61K 39/39* (2013.01);
(Continued)

(58) Field of Classification Search
None
See application file for complete search history.

(56) References Cited

U.S. PATENT DOCUMENTS 5,580,563 A * 12/1996 Tam .................. A61K 39/385
424/197.11
2004/0146484 A1    7/2004 Gaertner et al.
2007/0161088 A1 *  7/2007 Arumugham ...... A61K 39/0007
435/70.21

FOREIGN PATENT DOCUMENTS

CN       101503460 A    8/2009
EP       1195161 A2     4/2002
(Continued)

OTHER PUBLICATIONS

MI-AE, Kim et al., "Highly Cytokinergic IgE Antibodies and Autoimmune Mechanisms", Allergy Asthma and Immunology Research, vol. 4, No. 6, 2012 (p. 311).
(Continued)

*Primary Examiner* — M Franco G Salvoza
(74) *Attorney, Agent, or Firm* — Lucas & Mercanti, LLP

(57) ABSTRACT

The present invention provides a synthetic peptide capable of inducing an antibody to an autoantigen, and specifically, provides: a multiplexed same type-antigenic peptide having a dendritic core and B-cell recognition peptides, wherein the multiplexed same type-antigenic peptide comprises 4 to 8

(Continued)

B-cell recognition peptides of the same type that are bound to the terminal ends of the dendritic core directly or via a spacer, and each B-cell recognition peptide is bound to the terminal end of the dendritic core directly or via a spacer; an antibody production-inducing agent having the peptides; and a method for producing the peptide.

10 Claims, 7 Drawing Sheets

Specification includes a Sequence Listing.

(51) Int. Cl.
    *A61K 39/39*     (2006.01)
    *C07K 16/42*     (2006.01)
    *C07K 17/02*     (2006.01)
    *A61K 39/395*     (2006.01)
    *C07K 16/18*     (2006.01)

(52) U.S. Cl.
    CPC .......... *A61K 39/3955* (2013.01); *C07K 16/18* (2013.01); *C07K 16/42* (2013.01); *C07K 17/02* (2013.01); *A61K 2039/55522* (2013.01); *C07K 2317/34* (2013.01)

(56) References Cited

FOREIGN PATENT DOCUMENTS

| | | |
|---|---|---|
| JP | 2000502995 A | 3/2000 |
| JP | 2002281984 A | 10/2002 |
| JP | 2011057691 A | 3/2011 |
| WO | 9322343 A1 | 11/1993 |
| WO | 9720940 A1 | 6/1997 |
| WO | 0204497 A2 | 1/2002 |

OTHER PUBLICATIONS

Hovav, Avi-Hai et al., "Gamma Interferon and Monophosphoryl Lipid A-Trehalose Dicorynomycolate Are Efficient Adjuvants for Mycobacterium tuberculosis Multivalent Acellular Vaccine", Infection and Immunity, vol. 73, No. 1, 2005 (pp. 250-257).

Supplementary Partial European Search Report for the corresponding European Application No. 15806911.2 dated Dec. 4, 2017 (12 pages).

Christodoulides et al., "Immunization with a multiple antigen peptide containing defined B- and T-cell epitopes: production of bactericidal antibodies against group B Neisseria meningitidis", Microbiology, 1994, vol. 140, pp. 2951-2960.

Joshi et al., "Immunogenicity of Well-Characterized Synthetic Plasmodium falciparum Multiple Antigen Peptide Conjugates", Infection and Immunity, 2011, vol. 69, No. 8, pp. 4884-4890.

Oscherwitz et al., Synthetic Peptide Vaccine Targeting a Cryptic Neutralizing Epitope in Domain 2 of Bacillus anthracis Protective Antigen, Infection and Immunity, 2009, vol. 77, No. 8, pp. 3380-3388.

Simerska et al., "Development of a Liposacchadde-Based Delivery System and Its Application to the Design of Group A Streptococcal Vaccines", J.Med.Chem., 2008, vol. 51, pp. 1447-1452.

Zhong et al., "Development of highly pure alpha-helical lipoglycopeptides as self-adjuvanting vaccines", Tetrahedron, 2009, vol. 65, pp. 3459-3464.

Hayman et al., "Enhancing the immunogenicity and modulating the tine epitope recognition of antisera to a helical group A streptococcal peptide vaccine candidate from the M protein using lipid-core peptide technology", Immunology and Cell Biology, 2002, vol. 80, pp. 178-187.

Ponomarenko et al., "B-Cell Epitope Prediction", Structural Bioinformatics, 2009, Second Edition, pp. 849-879.

Sharon et al., "Discovery of protective B-cell epitopes for development of antimicrobial vaccines and antibody herapeutics", Immunology, 2013, vol. 142, pp. 1-23.

Singh et al., "Improved Method for Linear B-Cell Epitope Prediction Using Antigen's Primary Sequence" PLOS ONE, 2013, vol. 8, Issue 5, E62216, pp. 1-8.

Ball et al., "Induction of antibody responses to new B cell epitopes indicates vaccination character of allergen mmunotherapy", Eur. J. Immunol., 1999, vol. 29, pp. 2026-2036.

Robertson et al., "IgE Structure-Function Relationships Defined by Sequence Directed Antibodies Induced by Synthetic Peptides", Molecular Immunology, 1988, vol. 25, No. 2, pp. 103-113.

Falan et al., "Convergent synthetic methodology for the construction of self-adjuvanting lipopeptide vaccines using a novel carbohydrate scaffold", Bielstein J. Org. Chem., 2014, vol. 10, pp. 1741-1748.

International Search Report for International Application No. PCT/JP2015/066865 (dated Sep. 9, 2015) (6 Pages).

Joshi et al., "Immunogenicity of Well-Characterized Synthetic Plasmodium falciparum Multiple Antigen Peptide Conjugates", Infection and Immunity, 2001, vol. 69, No. 8, pp. 4884-4890.

Simerska et al., "Development of a Liposaccharide-Based Delivery System and Its Application to the Design of a Streptococcal Vaccines", J.Med.Chem., 2008, vol. 51, pp. 1447-1452.

Hayman et al., "Enhancing the immunogenicity and modulating the fine epitope recognition of antisera to a helical group A streptococcal peptide vaccine candidate from the M protein using lipid-core peptide technology", Immunology and Cell Biology, 2002, vol. 80, pp. 178-187.

Sharon et al., "Discovery of protective B-cell epitopes for development of antimicrobial vaccines and antibody therapeutics", Immunology, 2013, vol. 142, pp. 1-23.

Ball et al., "Induction of antibody responses to new B cell epitopes indicates vaccination character of allergen immunotherapy", Eur. J. Immunol., 1999, vol. 29, pp. 2026-2036.

Fagan et al., "Convergent synthetic methodology for the construction of self-adjuvanting lipopeptide vaccines using a novel carbohydrate scaffold", Bielstein J. Org. Chem., 2014, vol. 10, pp. 1741-1748.

International Search Report for International Application No. PCT/JP2015/066865 (dated Sep. 8, 2015) (6 Pages).

* cited by examiner

A

B

A

B

SEQUENCE LISTING

<160> NUMBER OF SEQ ID NOS: 3

<210> SEQ ID NO 1
<211> LENGTH: 14
<212> TYPE: PRT
<213> ORGANISM: Homo sapiens

<400> SEQUENCE: 1

Asp Trp Ile Glu Gly Glu Thr Tyr Gln Cys Arg Val Thr His
1               5                   10

<210> SEQ ID NO 2
<211> LENGTH: 14
<212> TYPE: PRT
<213> ORGANISM: Canis familiaris

<400> SEQUENCE: 2

Asp Trp Ile Glu Gly Glu Thr Tyr Tyr Cys Arg Val Thr His
1               5                   10

<210> SEQ ID NO 3
<211> LENGTH: 14
<212> TYPE: PRT
<213> ORGANISM: Mus musculus

```
<400> SEQUENCE: 3

Asp Trp Ile Glu Gly Tyr Gly Tyr Gln Cys Ile Val Asp His
1               5                   10
```

MULTIPLEXED SAME TYPE-ANTIGENIC PEPTIDE

CROSS-REFERENCE TO RELATED APPLICATIONS

This application is a 371 of PCT/JP2015/066865, filed Jun. 11, 2015, which claims the benefit of Japanese Patent Application No. 2014-120999, filed Jun. 11, 2014.

TECHNICAL FIELD

The present invention relates to a multiplexed same type-antigenic peptide, an antibody production-inducing agent containing the peptide, a method for producing the peptide, and a method for producing an antibody using the peptide.

BACKGROUND ART

An antibody binds to a foreign substance such as a virus or bacterium, or an autoantigen such as cancer cells in a body, thereby playing a major role in the immune response for eliminating them from the body. Because of this, a method for artificially and efficiently inducing in vivo production of antibodies to these substances as targets of the antibody reaction can be significantly used as therapeutic and prophylactic methods against infectious diseases, cancers or the like. However, at present, a method for efficiently producing an antibody to any types of antigen has not yet been developed, thereby many infectious diseases, cancers or the like that cannot be treated are still present.

In order to produce a class-switched antibody in vivo by differentiating B cells into plasma cells, firstly an antigen must be recognized by T cells. In other words, an antibody of interest cannot be produced if the reaction with T cells does not occur. Since the reaction with T cells depends on an antigen recognition pattern of the T cell receptor, T cells do not react with an antigen which does not fit the pattern (called "T cell restriction"). For example, in cancer immunotherapy or the like, it is difficult to induce an antibody to a cancer antigen, which is not clearly distinguished from an autoantigen. This is because T cells having the T cell receptor recognizing a cancer antigen, which is a part of autoantigens, have been eliminated basically in the thymus and do not exist in the body. Although the possibility of recognizing an autoantigen by B cells slightly remains, without interaction with such autoreactive T cells, the B cells cannot be activated and do not produce the autoantibody. As such, a method of administering an adjuvant, as a substance which forces T cells to recognize an antigen and to overcome the T cell restriction, together with a cancer antigen is employed at present. However, even if this method is employed, drastic effects on antibody production against such an antigen which basically T cells do not recognize has not yet been obtained.

A vaccine against an infectious disease can be generated if an antigen of pathogen is fully prepared. However, unless a culture system for providing a pathogen in a large scale is established, such a vaccine cannot be developed. Particularly, a vaccine against an emerging pathogens which mass culture system is still unknown cannot be prepared with this method. It will also require many years to establish an appropriate culture system. In addition, even if the mass culture method for a pathogen is established, in the case that the pathogen frequently and quickly mutates, in other words, the pathogen has a so-called genetic polymorphism for its pathogenic antigen, it will take time to adapt culture system to the mutation of pathogen and it is also difficult to overtake polymorphism.

Considering those issues above, development of synthetic peptide vaccines has been extremely focused in recent years. Of them, a multiple antigen peptide (MAP) has particularly attracted attention. MAP can be obtained by using, for example, a conjugate, as a core, containing a plurality of lysine (Lys) residues and optionally containing cysteine (Cys) residue which are one of amino acids to bind a peptide (a part of the antigen to be well recognized by cells) to an a amino group and an c amino group of Lys or to a sulfhydryl group of Cys.

For example, a MAP is used against *Diplococcus pneumoniae* in Patent Literature 1. Specifically, the literature describes that two sites are selected from an antigen peptide of *Diplococcus pneumoniae* and the two peptides are alternately arranged to form a MAP4 structure having four peptides in total.

Patent Literature 2 describes a multiple antigen peptide that has a T cell epitope bound therein and is capable of inducing both a humoral immune response and a cytotoxic T lymphocyte immune response.

Non-Patent Literature 1 describes as follows: a B cell epitope (a peptide region easily recognized by the B cell receptor or a membrane-bound antibody on the B cell surface) in antigen group B of *Neisseria meningitidis* and a T cell epitope (a peptide region recognized by T cell) were generated as synthetic peptides, both of which were combined to form a MAP. The MAP was administered concomitantly with an adjuvant to mice and rabbits and then an increase of the antibody titer was examined. As a result, the antibody titer did not increase in a MAP (MAP-8) obtained by binding eight same B cell epitopes; whereas, the antibody titer increased in a MAP (MAP-4) consisting of two identical B cell epitopes and two identical T cell epitopes.

Non-Patent Literature 2 describes that a MAP having a T cell epitope(s) for malaria parasite bound therein and a MAP having a T cell epitope(s) and a B cell epitope(s) in combination were generated inducing an antibody against the B cell epitope.

Non-Patent Literature 3 describes as follows: a MAP (MAP-4) having 4 same B cell epitopes for an anthrax antigen bound therein was used concomitantly with a Freund's adjuvant. To examine antibody production by the MAP, a rabbit model was selected, which was capable to forcibly recognize the epitope as a T cell epitope with the adjuvant. As a result, a neutralization antibody titer increased in the rabbits. In a mouse model, since the epitope was considered as a hapten or non-T cell epitope of mice, antibody production with the MAP was not expected.

In these findings of the prior arts, there is a common recognition that a MAP should be recognized by T cells to induce antibody against the MAP on the condition that T cell recognition of a peptide is inevitable to induce antibody production.

PRIOR ART LITERATURE

Patent Literatures

Patent Literature 1: JP Patent Publication (Kokai) No. 2011-57691
Patent Literature 2: International Publication WO1993/022343A1

Non-Patent Literatures

Non-Patent Literature 1: Myron Christodoulides and John E. Heckels, Microbiology 1994, 140: 2951-2960
Non-Patent Literature 2: Manju B. Joshi et al., Infection and Immunity 2001 69: 4884-4890
Non-Patent Literature 3: Jon Oscherwitz et al., Infection and Immunity 2009, 77: 3380-3388

SUMMARY OF INVENTION

Problem to be Solved by Invention

To produce a class-switched antibody arisen from B cells differentiating into plasma cells, it has been considered as being essential to carry out a set of processes: (1) that an antigen is incorporated into B cells via the B cell receptor (a membrane-bound antibody on the B cell surface) that binds to the antigen; (2) that a part of the antigen digested within the B cells (a T cell epitope) is presented to helper T cells; and (3) that the helper T cells recognize the T cell epitope and are activated to produce cytokine(s) and conversely stimulate the B cells presenting the antigen. Accordingly, variation of T cell epitopes limits antibody production.

Then, an object of the invention is to provide an immune stimulation method enabling to induce in vivo production of an antibody of interest by directly stimulating B cells without restriction on antigen recognition by T cells, and to provide a so-called vaccine.

Means for Solving Problem

As a result of intensive study with a view to overcoming the aforementioned problems, the present inventors have now found that, through using multiplexed artificial peptides having the same type of B-cell recognition peptides, production of a class switched antibody is induced in the absence of a T cell epitope by directly stimulating B cells in vivo without forcibly inducing T cells which recognize the peptide in the body with the use of an adjuvant or the like.

Since the artificial peptides having such a structure was found to induce antibody even without T cell epitope, production of antibodies to any peptides can be easily obtained by using the peptides. In addition, an antibody to an antigenic region against which it has been difficult to induce production of an antibody (for example, autoantigen) due to the restriction on recognition by helper T cells has been successfully induced in vivo.

To sum up, the present invention encompasses the following features.

(1) A multiplexed same type-antigenic peptide comprising a dendritic core and B-cell recognition peptides, wherein the multiplexed same type-antigenic peptide comprises 4 to 8 B-cell recognition peptides of the same type, which are bound to the terminal ends of the dendritic core directly or via a spacer, and production of a class-switched antibody is induced by directly stimulating B cells in vivo in the absence of a T cell epitope.

(2) The multiplexed same type-antigenic peptide according to the above (1), wherein the dendritic core comprises lysine residues.

(3) The multiplexed same type-antigenic peptide according to the above (2), wherein the dendritic core further comprises a cysteine residue.

(4) The multiplexed same type-antigenic peptide according to any one of the above (1) to (3), wherein the B-cell recognition peptide is a peptide consisting of 7 to 50 amino acid residues.

(5) The multiplexed same type-antigenic peptide according to any one of the above (1) to (4), wherein the B-cell recognition peptide is an autoantigen.

(6) The multiplexed same type-antigenic peptide according to the above (5), wherein the autoantigen is an antigen derived from IgE.

(7) An antibody production-inducing agent containing the multiplexed same type-antigenic peptide according to any one of the above (1) to (6) as an active ingredient.

(8) The antibody production-inducing agent according to the above (7), further comprising interferon γ and/or an adjuvant having an ability to produce interferon γ.

(9) The antibody production-inducing agent according to the above (7) or (8), wherein the antibody is an IgG antibody.

(10) The antibody production-inducing agent according to any one of the above (7) to (9), wherein the antibody production-inducing agent is a vaccine.

(11) The antibody production-inducing agent according to any one of the above (7) to (10), which is for use in treating or preventing a disease.

(12) The antibody production-inducing agent according to the above (11), wherein the disease is selected from the group consisting of allergic diseases, cancers, bone diseases, age-related macular degeneration, multiple sclerosis, psoriasis vulgaris, and infections.

(13) A pharmaceutical composition comprising the antibody production-inducing agent according to any one of the above (7) to (12).

(14) A method for producing the multiplexed same type-antigenic peptide according to any one of the above (1) to (6), comprising the following steps (a) to (d):

(a) a step of providing a dendritic core having reactive functional groups;
(b) a step of providing a plurality of the same type of B-cell recognition peptides having reactive functional groups;
(c) a step of effecting a binding reaction of the reactive functional group of the dendritic core with the reactive functional group of each B-cell recognition peptide to prepare the multiplexed antigenic peptide; and
(d) a step of collecting the multiplexed antigenic peptide.

(15) The method according to the above (14), wherein the dendritic core having reactive functional groups has the following structure:

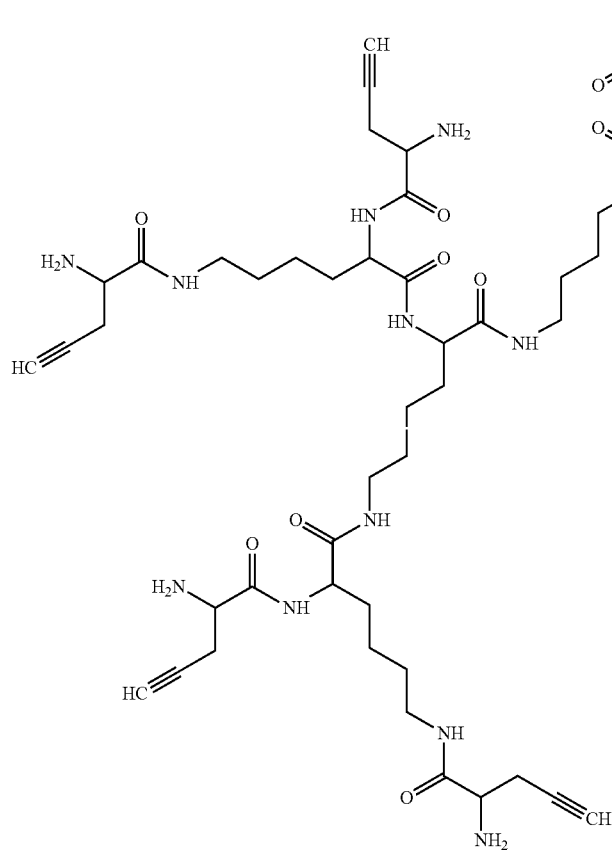

(16) The method according to the above (14) or (15), wherein the binding reaction of the reactive functional group of the dendritic core with the reactive functional group of the B-cell recognition peptide is effected by the Huisgen reaction.

(17) A method for producing an antibody comprising the following step (a):

(a) a step of administering the multiplexed same type-antigenic peptide according to any one of the above (1) to (6) to a subject.

(18) The method according to the above (17), further comprising the following steps (b) to (d):

(b) a step of obtaining a biological sample containing B cells that produce an antibody binding the B-cell recognition peptide of the multiplexed same type-antigenic peptide, from the subject administered;

(c) a step of selecting the B cells from the biological sample obtained in the step (b); and (d) a step of culturing the B cells and collecting the antibody.

(19) A method for screening for an antibody that binds to a B-cell recognition peptide of the multiplexed same type-antigenic peptide according to the above (1), from a biological sample obtained from a subject to which the multiplexed same type-antigenic peptide has been administered.

(20) A method for collecting an antibody that binds to a B-cell recognition peptide of the multiplexed same type-antigenic peptide according to the above (1), from a biological sample obtained from a subject to which the multiplexed same type-antigenic peptide has been administered.

(21) A method for preparing an IgG antibody that recognizes an allergen and suppresses production of IgE, comprising the following steps (a") and (b").

(a") a step of administering the multiple antigen peptide according to any one of the above (1) to (6) comprising B-cell recognition peptides that consist of a part of an allergen structure, to a subject;

(b") a step of obtaining a biological sample from the subject administered and collecting the IgG antibody recognizing the allergen.

(22) A method for identifying the gene sequence for or the amino acid sequence of an antigen recognition site of an antibody from antibody-producing B cells obtained by administering the multiple antigen peptide according to any one of the above (1) to (6) to a subject.

According to the present invention, since antibodies can be produced in vivo without restriction on antigen recognition by T cells, the success rate of antibody production, particularly the success rate of production of antibodies to an autoantigen, is improved compared to the conventional antibody production technology. The production of an antibody by using the multiplexed same type-antigenic peptide of the present invention can be used for treating and/or preventing diseases.

An antibody drug already available in the art is required for consecutive administration because of its transient effect; whereas, in the present invention, antibodies can be induced to an autoantigen and the effect of the antibodies is expected to extend over a long term. An antibody pharmaceutical preparation, even if the antibody is a humanized antibody, is regarded as a foreign substance for the body of human. Because of this, as being frequently administered, neutralization antibodies to the antibody pharmaceutical preparation occur in the body, resulting in reduction of the effect of the antibody pharmaceutical preparation. In contrast, such a phenomenon does not occur in antibody induction of the present invention and a desired antibody production can be stimulated with every injection.

The contents described in the specification and/or the drawings of JP patent application No. 2014-120999 from which the present application claims the priority, are included herein.

MODE FOR CARRYING OUT THE INVENTION

Figure 1:
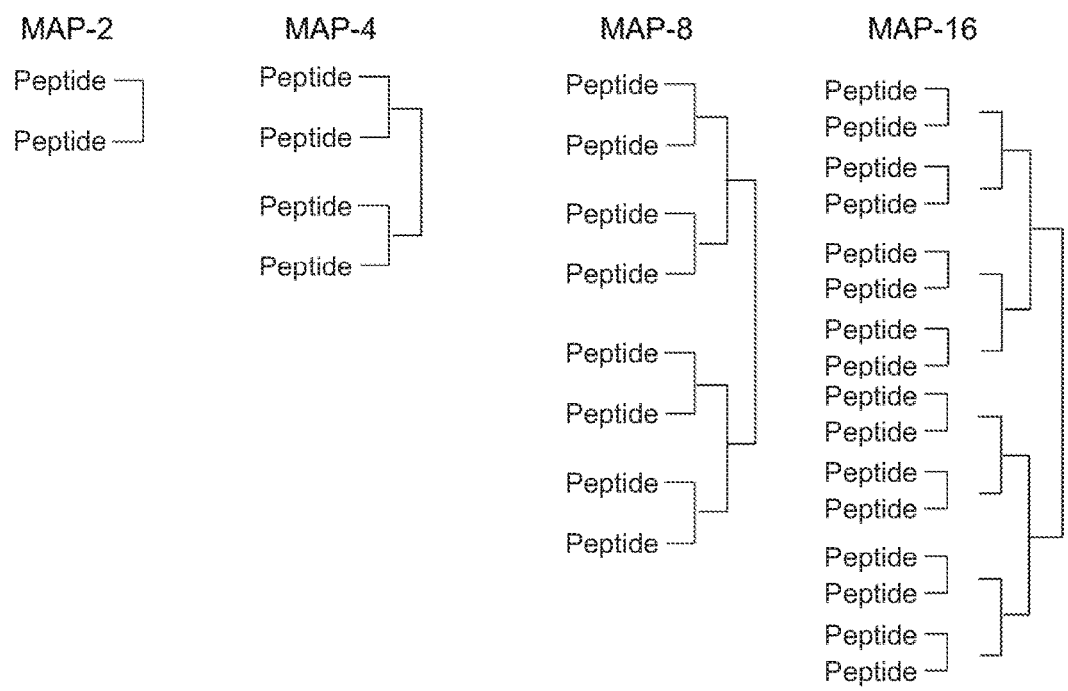
FIG. 1 This figure illustrates the structures of MAPs (MAP-2, MAP-4, MAP-8 and MAP-16).

The present invention will be described in more detail.
1. Multiplexed Same Type Antigenic Peptide According to the first embodiment, the present invention provides a multiplexed same type-antigenic peptide comprising a dendritic core and B-cell recognition peptides, wherein the multiplexed same type-antigenic peptide comprises 4 to 8 B-cell recognition peptides of the same type that are bound to the terminal ends of the dendritic core directly or via spacer, and a class-switched antibody is induced in vivo by directly stimulating B cells in the absence of a T cell epitope.

The "Multiplexed same type-antigenic peptide" (MAP) used hereon is a polymer substance that comprises a dendritic core, which has a dendritic polymer (i.e., dendrimer) structure, and a plurality of the same type B-cell recognition peptides, wherein the B-cell recognition peptides are bound directly or via spacer to the terminal ends of the dendritic core.

The dendritic core is a dendritic support core for binding a plurality of B-cell recognition peptides (hereinafter referred to also as "antigen peptide" conveniently) and preferably 4 to 8 B-cell recognition peptides. The dendritic core may have a structure commonly known. As the dendritic polymer, a dendritic polymer basically having two or more identical branches that are extended from a core molecule having at least two functional groups is preferably selected. As the dendritic core, which is also called dendritic polymer, the structures, which are described, for example, in U.S. Pat. Nos. 4,289,872 and 4,515,920, can be included but are not limited thereto. The dendritic core is preferably a peptide containing a plurality of lysine residues (K) in view of simplicity in manufacturing. The peptide containing lysine residues may further contain a cysteine residue (C). In the case of e.g., the K-K-K structure consisting of three lysine residues (K), a single B-cell recognition peptide can be bound to the α-amino group and ε-amino group sides of each terminal lysine residue (K). In this case, at most four B-cell recognition peptides can be bound. A spacer may be bound to a lysine residue (K) via α-carboxyl group of the lysine residue. The spacer is a peptide consisting of preferably 2 to 10 amino acid residues and can include, for example, K-K-C, K-βA-C (where βA represents a β-alanine residue and C represents a cysteine residue). For example, in the case of a lysine residue (K), the K-K-K-structure having at most four B-cell recognition peptides bound in the same manner as above, can be connected to the amino acid group at the N-terminus of a spacer via the α-amino group of the lysine residue. In this case, the generated MAP has at most 8 B-cell recognition peptides.

The B-cell recognition peptide is recognized by the B cell receptor and serves as an antigen segment that determines antigenicity. The B-cell recognition peptide consists of seven or more amino acids arbitrarily selected from the amino-acid sequence information of a protein of interest and is preferably a peptide of continuous amino acids (or a linear epitope) on the surface of a protein. The B-cell recognition peptide may be a peptide that constructs the conformation of a protein recognized by the B cell receptor, or may be, for example, a selected discontinuous combination of adjacent peptides (or a conformational epitope) on the surface of a protein.

The linear epitope consists of a continuous primary amino acid sequence in specific region of an antigenic protein, and specifically binds to an antibody to the epitope. On the other hand, the conformational epitope is, for example, a combination of peptides independently forming two or more configurations adjacent to each other on the surface of a protein. These peptides are discontinuously present in the primary amino acid sequence of an antigenic protein. Two or more peptides having such relationship are combined to form a conformational epitope and the antibody to the epitope specifically recognizes and binds to the higher-order structure of the antigenic protein.

As used herein, the B-cell recognition peptide can be referred to as a B cell epitope in that it is an antigen segment that is recognized by the B cell receptor and determines antigenicity. Hereinafter, the B-cell recognition peptide is optionally described as the "B cell epitope" conveniently. Since the B-cell recognition peptide differs, in most cases, from a T cell epitope, which binds to the T cell receptor and refers to an antigen portion recognized by T cells, the B-cell recognition peptide generally has a property of being not mediated by T cells. In general, the T cell epitope that is a part of antigen-presented by antigen-presenting cells is known to bind to the T cell receptor (TCR) to activate helper T cells, resulting in the cellular immunity or the humoral immunity. In contrast, the B-cell recognition peptide (or B cell epitope), which is not antigen-presented to the TCR, binds to the B cell receptor (BCR), thereby contributing to the production process of an antibody and thus being involved in only the humoral immunity.

The B-cell recognition peptide may have an amino acid sequence consisting of typically 7 to 50 amino acids, preferably 10 to 20 amino acids, and more preferably 12 to 16 amino acids.

The B-cell recognition peptide preferably corresponds to a portion exposed on the surface of proteins (including metabolites in the living body). Thus, the B-cell recognition peptide can be designed by those skilled in the art by arbitrarily selecting a portion exposed on the surface of biological macromolecules, such as proteins, based on analysis results or prediction results concerning amino acid sequences, conformations, and the like of target proteins recognized by antibodies. For example, a variety of prediction methods known in the art may be used. Such prediction methods are specifically described in Julia V. Ponomarenko and Marc H. V. van Regenmortel, "B-Cell Epitope Prediction" (edited by Jenny Gu and Philip E. Bourne, Structural Bioinformatics, Second Edition, 2009 John Wiley & Sons, Inc.). In this literature, the following 4 methods are disclosed: (1) sequence-based methods; (2) amino acid scale-based methods; (3) a structure-based methods; and (4) protein-protein binding site prediction methods.

The sequence-based method is limited to prediction of continuous epitopes. This method is mostly based on the hypothesis that an epitope must be a part being accessible by an antibody in order to bind to the antibody. Accordingly, this method relies upon use of epitope properties involved in the surface exposure of epitopes.

In the amino acid scale-based method, the score of a specific amino acid residue in predetermined protein sequence is computed using the amino acid scale. The final score of the amino acid residue is an average of scale values to the number of amino acids in windows. Specifically this method includes the ABCpred method using artificial neural network (S. Saha and G P Raghava, Proteins 2006, 65 (1): 40-48) and the BepiPred method based on the combination of the hidden Markov model and the two amino acid scale (J E Larsen et al., Immunome Res., 2006, 2: 2).

The structure-based method is a method based on the three-dimensional structure of an antigen. Two methods, CEP (U. Kulkarni-Kale et al., Nucleic Acids Res 33: W168-W171) and DiscoTope (P. H. Andersen et al., 2006, Protein Sci 15 (11): 2558-2567), are known.

The protein-protein binding site prediction method includes, for example, PPI-PRED method (J. R. Bradford et al., Bioinformatics 2005, 21 (8): 1487-1494).

In the conventional methods, a portion which will serve as a T cell epitope has to be considered in addition to a B cell epitope. In contrast, according to the present invention, production of a class-switched antibody (preferably, antigen-specific IgG) recognizing the epitope can be induced by merely designing a single epitope.

The B-cell recognition peptide of the present invention can be selected from the peptide region which cannot be B cell epitopes usually in nature, in addition to peptide region serving as known B cell epitopes. Thus, a novel B cell epitope can be artificially induced in addition to known B cell epitopes. An IgG related suppressive signal to novel B cell epitope can be introduced into memory B cells, which have a membrane-bound IgG recognizing a conventional B cell epitope on the cell surface, and mast cells having a similar membrane-bound IgE on the cell surface. Owing to this, an autoimmune disease can be treated by suppressing antibody-producing B cells that have already exist, and allergy can be treated by suppressing degranulation of mast cells.

A first feature of the MAP of the present invention is that the B-cell recognition peptide is bound to the terminal ends of the aforementioned dendritic core directly or via a spacer (preferably, covalently bound to each of the terminal ends one by one). For example, the functionalized dendritic core is bound to a functionalized solid-phase resin, and the reactive functional group of the B-cell recognition peptide can be bound to reactive functional groups of the dendritic ends (W. Kowalczyk et al., J. Pep. Sci. 2011, 17: 247-251). In this case, the B-cell recognition peptide can be synthesized by a known technique, for example, by using an automatic peptide synthesizer or the like based on predetermined amino acid sequences (J. M. Stewart and J. D. Young, Solid Phase Peptide Synthesis, $2^{nd}$ ed., Pierce Chemical Company, 1984, G. B. Fields et al., Principles and Practice of Peptide Synthesis, in G. A. Grant (ed): Synthetic Peptides: A User's Guide, W. H. Freeman, 1992).

The MAP of the present invention comprises a plurality of B-cell recognition peptides, preferably 4 to 8 B-cell recognition peptides. The individual peptides are identical or have a high identity with one another. The peptides may be known B cell epitopes or entirely new epitopes. As used herein, the "B-cell recognition peptide of the same type" means: a peptide having the same nature as an epitope, including a peptide having a high identity. The "peptide having a high identity" means a peptide having a sequence identity of from 85% or more, preferably 90% or more, more preferably 95% or more to 100% with any one of a plurality of B-cell recognition peptides; or a peptide having 1 to 4 different amino acids, preferably 1 to 3 different amino acids, more preferably 1 to 2 different amino acids and further preferably a single different amino acid in terms of difference in the number of amino acids between the amino acid sequences of the peptides. Herein, the "the same nature as an epitope" refers to a property of being capable of inducing in vivo production of an antibody capable of binding to a target protein or polypeptide. The "difference" regarding amino acids means a difference in the number of amino acids caused by substitution, deletion or addition of amino acids.

The second feature of the MAP of the present invention is that the B-cell recognition peptide is a peptide from either an autoantigen or a non-self antigen, preferably from an autoantigen.

As used herein, the "autoantigen" means a gene product, which is common among the same species as the subject that the MAP of the invention is administered to, or a metabolite derived from the gene product, wherein the gene product or the metabolite includes both syngeneic and allogeneic. Accordingly, the B-cell recognition peptide can be designed based on known gene information of the same species as the subject to be administered, even if genetic information of individual subjects to be administered is not decoded. Even if gene products are the same, in the case where the amino acid sequences of the gene products differ due to a variation such as single nucleotide polymorphism, the MAP of the present invention may be designed for administration on the basis of individual genetic information that each subject has. The design is optimized to each individual but its general versatility is lost. In such a view point, the known genetic information of the same species is deemed as the allogeneic information; however as long as the genetic information is from the same species, a B-cell recognition peptide having high identity in the species can be designed. Accordingly, the B-cell recognition peptide based on such information is also treated as a peptide derived from the "autoantigen."

In the case where the B-cell recognition peptide is derived from an autoantigen, the antibody induced by the present invention becomes an autoantibody.

Examples of the gene product include, but are not limited to, antibodies, cytokines, growth factors, transmembrane proteins, and cell surface proteins. In addition, all of antigens derived from tumor cells, antigens such as tumor-producing factors, and factors derived from self-gene products directly or indirectly involved in diseases are included as the autoantigen herein.

Specific examples thereof will be further described below.

Specifically, examples of the autoantibody capable of inducing according to the present invention include, but are not limited to, antibodies to IgE. The MAPs of the invention having IgE-derived B-cell recognition peptides can be used for treating or preventing allergic diseases such as asthma, pollinosis (or hay fever), and food allergy.

Specific examples of the cytokine include, but are not limited to, TNFα and IL-1β. The MAPs of the invention having TNFα-derived B-cell recognition peptides can be used for treating or preventing articular rheumatism. The MAPs of the invention having IL-1β-derived B-cell recognition peptides can be used for treating or preventing the cryopyrin-associated periodic syndrome.

Specific examples of the growth factor include, but are not limited to, vascular endothelial cell growth factor (VEGF). The MAPs of the invention having VEGF-derived B-cell recognition peptides can be used for treating or preventing a cancer such as colorectal cancer, or an age-related macular degeneration.

Specific examples of the transmembrane protein include, but are not limited to, epithelial growth factor receptor (EGFR), receptor activator of nuclear factor-κB ligand (RANKL), α4 integrin, CD2, CD3, CD11, CD20, CD25, CD30, CD33, CD52 and CD152 (CTLA4). The MAPs of the invention having EGFR-derived B-cell recognition peptides can be used for treating or preventing cancers such as head and neck cancer and colorectal cancer. The MAPs of the invention having a RANKL-derived B-cell recognition peptide can be used for treating or preventing bone diseases such as bone lesions and osteoporosis. The MAPs of the invention having α4 integrin-derived B-cell recognition peptides can be used for treating or preventing multiple sclerosis. The MAPs of the invention having CD2-derived B-cell recognition peptides can be used for treating or preventing psoriasis vulgaris. The MAPs of the invention having CD3-derived B-cell recognition peptides can be used for treating or preventing an acute rejection. The MAPs of the invention having CD11-derived B-cell recognition peptides can be used for treating or preventing psoriasis vulgaris. The MAPs of the invention having CD20-derived B-cell recognition peptides can be used for treating or preventing cancers such as non-Hodgkin's lymphoma and chronic lymphocytic leukemia. The MAPs of the invention having CD25-derived B-cell recognition peptides can be used for treating or preventing acute rejection. The MAPs of the invention having CD30-derived B-cell recognition peptides can be used for treating or preventing a cancer such as Hodgkin's lymphoma. The MAPs of the invention having CD33-derived B-cell recognition peptides can be used for treating or preventing a cancer such as acute myeloid leukemia. The MAPs of the invention having CD52-derived B-cell recognition peptides can be used for treating or preventing a cancer such as B-cell chronic lymphocytic leukemia. The MAPs of the invention having CD152-derived B-cell recognition peptides can be used for treating or preventing a cancer such as melanoma.

Specific examples of the cell surface protein include, but are not limited to, HER2. The MAPs of the invention having HER2-derived B-cell recognition peptides can be used for treating or preventing a cancer such as breast cancer.

As used herein, the "non-self antigen" means an epitope contained in a gene product not commonly present in the same species as the subject to which the MAP of the present invention is to be administered, or contained in a metabolite derived from the gene product, and includes a foreign substance to the subject to be administered or the same species of the subject. Examples of such non-self antigen include antigens derived from pathogens such as bacteria and viruses. According to the present invention, at the time point when the structure of a target pathogen is found, the MAP can be designed and generated by merely selecting a peptide that can serve as an epitope. Because of this, it is not necessary to establish a method for culturing the pathogen.

According to the present invention, it is possible to induce an antibody recognizing a region which cannot be a B cell epitope in nature. The IgG recognizing the new B cell epitope can bind to the IgG receptor of B cells or mast cells while keeping the binding with the antigen in vivo. This feature can be used in therapeutic or prophylactic drugs for suppressing allergic symptoms in accordance with the mechanism of original antigenic sin.

More specifically, even if B cells have a membrane-bound antibody recognizing the same antigen or even if IgE recognizing the antigen is bound to the surface of mast cells, an antibody recognizing a new B cell epitope binds to the IgG receptor on the surface of B cells or mast cells. Because of this, the signal for suppressing activation is capable of being transmitted to the B cells or the mast cells. The B cells, which have received the activation suppressing signal, can no longer be activated and thus cannot produce any antibodies. Accordingly, this effect can be used in therapeutic or prophylactic drugs for suppressing an autoantibody-producing B cells. Similarly, since mast cells cannot be de-granulated, this action can be used in therapeutic or prophylactic drugs for suppressing allergic symptoms.

As used herein, the "subject to which the multiplexed same type-antigenic peptide is administered" (hereinafter referred to also as a "subject" conveniently) includes human, domestic animals (e.g., cow, pig, poultry and camel), companion animals (e.g., dog, cat and bird), racing animals (e.g., horse), and mammals such as ornamental animals that are raised in zoos, preferably human.

A third feature of the MAP of the present invention is that the MAP induces production of a class switched antibody without being mediated by T cells in the body of a subject.

As used herein, the "without being mediated by T cells" means that production of antibodies to the MAP is induced by directly acting on the B cell receptor without mediating the normal immune system, which directs the cellular immunity and the humoral immunity through binding to the T cell receptor as in T cell epitopes.

The antibodies produced by the present invention are IgG, IgA and IgE, preferably IgG. Inducing IgG production without being mediated by T cells is important. Generally, when a foreign substance enters the body, IgM antibody is produced within about a first week and initial defense works in the body; however, the half-life of IgM is short and thus the antibody titer of IgM in blood decreases at a period from a week to 10 days. After the IgM production, gradually T cells reacting with the foreign substance are activated in the body to normally produce interferon γ, thereby leading to production of IgG antibodies to strengthen defense by the humoral immunity. IgG, once produced, lasts long (i.e., having a long half-life) and the antibody titer thereof in blood is maintained for a period from a few weeks to a few months or more. The B-cell recognition peptide of the present invention is a peptide region that B cells recognize, that is, a known B cell epitope or a newly found B cell epitope. Since the B-cell recognition peptide is not related to T cell recognition, it has been said that any immunoglobulin class-switch from IgM to IgG does not occur in case of only B cell epitopes; however, it has been now demonstrated that the B cells stimulated by the MAP, while stimulated by non-specific interferon γ constantly produced in the body, can produce specific IgG. As such, when the MAP is administered to a subject concomitantly with interferon γ or an interferon γ inducing substance, surely B cells produce IgG.

The MAP of the present invention has, for example, any of the structures as shown in FIG. 1, particularly a dendritic structure comprising 4 to 8 B-cell recognition peptides of the same type, preferably identical B-cell recognition peptides, as shown in MAP-4 or MAP-8. Examples for producing the MAP will be described below.

2. Production of Multiplexed Same Type-Antigenic Peptide

According to the second aspect, the present invention provides a method for producing the MAP as mentioned above, comprising the following steps (1) to (4):

(1) a step of providing a dendritic core having reactive functional groups, (2) a step of providing a plurality of B-cell recognition peptides of the same type having reactive functional groups, (3) a step of effecting a binding reaction of the reactive functional group of the dendritic core with the reactive functional group of each B-cell recognition peptide to prepare a multiple antigen peptide; and (4) a step of collecting the multiple antigen peptide.

The dendritic core is a dendritic support core for binding a plurality of B-cell recognition peptides of the same type, preferably 4 to 8 B-cell recognition peptides of the same type, preferably identical peptides, as described above. The dendritic core may have a commonly known structure, preferably may comprise a plurality of lysine residues (K), and may further comprise a cysteine residue (C). In the structure of the MAP of the present invention illustrated in FIG. 1 (preferably, the structures such as MAP-4 and MAP-8), the dendritic core is formed of the portion except 4 to 8 B-cell recognition peptides (i.e., B cell epitopes). In the case of MAP-4, the dendritic core preferably contains e.g., a K-K-K sequence, while in the case of MAP-8, the dendritic core preferably contains e.g., a K-K-K-K-K sequence. At the center K of these sequences, a spacer is usually bound. The spacer is a peptide consisting of preferably two or more amino acid residues, for example, represented by K-K-C or K-βA-C (where the βA represents a β-alanine residue): but the peptide is not limited to this. A design is conducted so that two B-cell recognition peptides per K are bound to each of the right and left K or K-K except the center K.

Each end of the dendritic core may have a functional group for appropriately binding to a B-cell recognition peptide. As the functional group, any functional group may be used as long as it can be used for modifying a protein, and examples of the functional group include amino group, sulfhydryl group, acetylene group, and N-hydroxysuccinimidyl group.

On the other hand, the functional group in the B-cell recognition peptide is any functional group capable of causing the reaction of binding to the terminal functional group of the dendritic core, and examples of the functional group include N-hydroxysuccinimidyl group reactive to amino group, sulfhydryl group or carboxyl group reactive to sulfhydryl group, and azido group reactive to acetylene group. The B-cell recognition peptides are as described above.

According to the embodiment of the present invention, the terminal functional group of the dendritic core having a K-K-K sequence may have the following structure having acetylene groups:

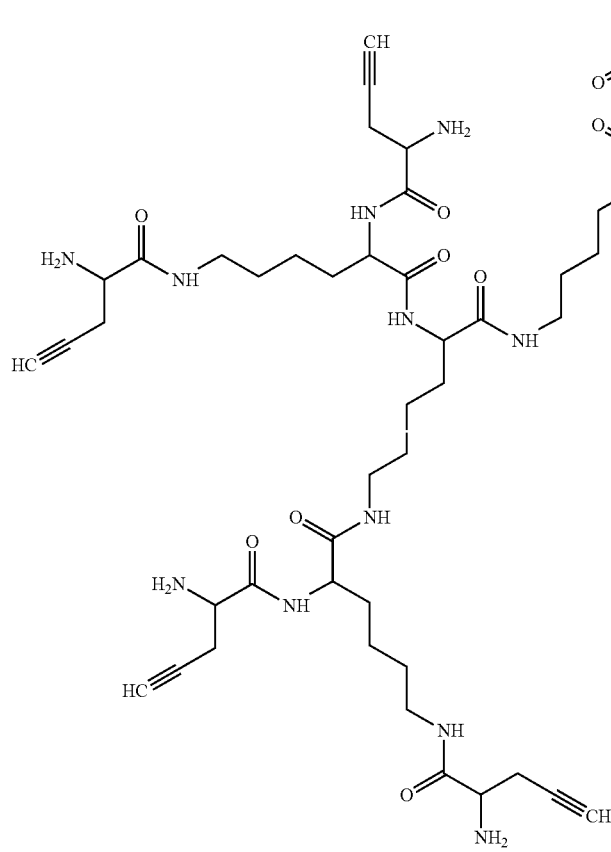
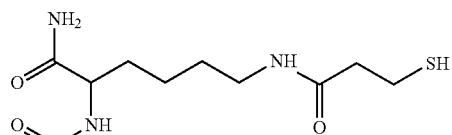

The terminal functional group of the B-cell recognition peptide having the above structure is an azido group. In this case, the binding reaction is the Huisgen reaction. In this reaction, an alkyne and an azide are bound in the presence of a monovalent copper ion as a catalyst. The resultant reaction product is stable and substantially free from side reactions. This reaction attracts attention as click chemistry. The solution of the copper ion catalyst may be prepared by using an aqueous solution of copper sulfate pentahydrate and ascorbic acid. A specific example of the reaction is described in Example 2 described later.

In the step of collecting the MAP, the peptide is purified. A method for collecting the peptide may be a general purification method for proteins or polypeptides, including, for example, chromatography methods such as gel filtration chromatography, ion exchange chromatography, hydrophobic interaction chromatography, reverse phase chromatography, affinity chromatography, and high performance liquid chromatography (HPLC), which may be used alone or in combination. The peptide product can be identified by use of nuclear magnetic resonance spectroscopy NMR, mass spectroscopy, amino acid analysis, and the like.

3. Antibody Production-Inducing Agent

According to the third aspect, the present invention provides an antibody production-inducing agent comprising the MAP as mentioned above. The antibody production-inducing agent of the invention is a preparation that induces production of a class-switched antibody without being mediated by T cells.

The antibody production-inducing agent of the invention can be used for treatment or prevention of a disease as a pharmaceutical composition, by significantly inducing production of an antibody, and as a "vaccine" for therapeutic and/or prophylactic purpose.

The antibody production-inducing agents of the invention can be classified into, for example, the following (a), (b) and (c).

(a) Antibody Production-Inducing Agent for Autoantibody Induction

The antibody production-inducing agent of the present invention can artificially induce antibodies to an autoantigen (i.e., autoantibodies), in which production of antibodies are restricted by T cells, as in a manner independent of T cells in the body. Production of autoantibodies can be used to eliminate molecules irrelevant to health maintenance from the body. Many tumor cells excessively produce an antigen which is only slightly expressed in normal cells, and such antigen is released in the bloodstream or remains on the cell surface. Immune response to the tumor antigens has diversity and is often insufficient to suppress tumor growth. The antibody production-inducing agent of the invention is capable of inducing antibodies to a tumor antigen.

(b) Antibody Production-Inducing Agent for a Disease Against which a Vaccine was Unable to be Prepared A chemically synthesized product-based vaccine preparation can be developed at the time point when the structure of a bacterium or virus as an infectious source is revealed, and the vaccine is significantly different in speed of developing vaccines from the conventional technique in which a method for culturing an infectious source is first established and then the process goes to development of a vaccine preparation. This feature shows that vaccine preparations suitable for an infection, which has not been able to be dealt with conventional techniques, and a newly emerged infection can be generated.

(c) Antibody Production-Inducing Agent Capable of Dealing with a Foreign Substance The present invention can be said to be a method that can easily induce production of an intended antibody to a foreign substance by chemical synthesis. It is possible to artificially induce an antibody in a planned manner to a site against which an antibody cannot be generated in a conventional manner. Specifically, in a conventional technique, it was only possible to produce a vaccine inducing an antibody to an influenza virus only against a high antigenicity region at which a mutation easily occurs; however, production of an antibody against a low antigenicity region where mutation does not occur can be potently induced by the present invention.

In the present invention, peptide region having homologous amino acid sequences or highly identical amino acid sequences are selected in a highly conserved protein or polypeptide in a human or an animal other than human. In this way, the safety and efficacy for human can be directly demonstrated by animal experimentations. This further means that the present invention can be applied not only to human drugs but also to veterinary drugs, and the present invention can be said to have a wide range of applications.

Since in the present invention a chemically synthesized peptide is formulated in the form of a preparation, it is possible to provide the preparation at the time when the structure of a pathogen was clarified. Due to chemical synthesis, it is not required to establish a method for culturing a pathogen. Furthermore, since B cells are forced to induce antibody production, the sequence of a peptide serving as an antigen recognition region can be freely set. These facts mean that a vaccine against a newly emerged infectious disease can be developed and that a vaccine inducing antibodies to a constant region having no variation of a virus frequently causing mutations can be developed. For example, the present invention can be dealt with viral diseases that a conventional technique cannot deal with, such as West Nile fever, Ebola hemorrhagic fever, influenza, and foot-and-mouth disease. Furthermore, in the present invention, since in the present invention it is possible to provide the preparation at the time when the structure of a pathogen was clarified, if an antigenic variation is found, then needless to say, a peptide can be designed against the variation in the same manner as above to successfully provide the antibody production-inducing agent of the present invention.

The present inventors have thought of a multiple antigen structure as a T cell-independent antigen. The target peptide against which an antibody is to be induced is provided by chemical synthesis. Two to sixteen synthetic peptides thus generated are bound to a dendrimer by chemical synthesis (MAP-2 to MAP-16). In one of the Examples described later, IgE was selected as a target molecule for antibody induction and, further a part of the CH3 region highly identical among human, mouse, and dog was selected. This was administered to mice and dogs, and a degree of increase in autoantibody was examined. First of all, the number of peptides to be bound to a MAP was examined. Since the increase in antibody level was observed in MAP-4 and MAP-8, the number of peptides for obtaining the effect of the invention was determined as 4 to 8.

The non-limiting effective amount of the MAP of the present invention per dose in a human is, in the case of MAP-4, about 0.05 to 2.5 μg/kg body weight to 1 mg to 10 mg/kg body weight and, in the case of MAP-8, 0.5 to 25.0 μg/kg body weight to 1 mg to 10 mg/kg body weight. The dosage herein can be appropriately changed depending upon the body weight, age, gender and symptom of a subject including human, type of disease, severity, and administration method.

To examine whether an increased antibody is an autoantibody to mouse IgE or whether the increased antibody is an antibody to a sequence site that is non-self for mouse (where it is a sequence site of a dog or human), inhibition tests using a dog IgE reagent (Bethyl Laboratories) were conducted. As a result, it was confirmed that the autoantibody to mouse IgE was produced, that the antibody to non-self sequence was produced, and that both of the autoantibody and the antibody to foreign antigen were induced by the MAP.

The isotype of the antibody increased in a T cell-independent manner by the present invention is preferably IgG. The induction of IgG is likely to be due to the action of interferon γ produced from T cells in a non antigen-specific manner. In order to demonstrate the concept, MAP-4 and interferon γ were administered to mice (nude mice) having no T cells. As a result, the T cell-independent antibody (IgG) production was confirmed by antigen-nonspecific interferon γ. Accordingly, it is preferable that the antibody production-inducing agent of the present invention comprises interferon γ.

The antibody production-inducing agent of the present invention is in the form of, for example, solution, suspension, tablets, injection, granules, emulsifier, or the like and may appropriately contain an additive or additives such as excipient, diluent, binding agent, flavoring agent, surfactant, and the like. An adjuvant is not basically required as long as interferon γ is produced in the subject to be administered; however, an adjuvant is added where required.

The antibody production-inducing agent of the present invention preferably comprises interferon γ or an adjuvant having an ability to produce interferon γ. Examples of the adjuvant having an ability to produce interferon γ include; but are not limited to, α-galactosylceramide, α-galactosylceramide analogues, CpG which is a bacterial oligonucleotide, and aluminum hydroxide (Alum). Examples of the α-galactosylceramide analogues include; but are not particularly limited to, compounds described in, for example, International Publication WO2007/099999 (U.S. Pat. No. 8,163,705), International Publication WO2009/119692 (U.S. Pat. No. 8,551,959), International Publication WO2008/102888 (U.S. Pat. No. 8,299,223), International Publication WO2010/030012 (U.S. Pat. No. 8,580,751), International Publication WO2011/096536 (U.S. Pat. No. 8,853,173) and International Publication WO2013/162016 (U.S. Publication No. 2015-0152128 A1). Note that, all the compounds described in these literatures are incorporated herein as examples of the α-galactosylceramide analogues, as a part of the disclosure. In the case where IgA is dominantly produced, an adjuvant is a beta-type transforming growth factor (TGF-β) or a substance dominantly inducing TGF-β production. Examples of the substance dominantly inducing TGF-β production include, but are not particularly limited to, Cholera Toxin subunit B, retinoic acid and the like. In the case where IgE is dominantly produced, a cytokine such as interleukin-4 or interleukin-13 or a substance dominantly inducing production of the cytokine is used. The substance dominantly inducing production of a cytokine such as interleukin-4 or interleukin-13 includes, but are not particularly limited to, forskolin, Der p 1 (a main allergen of mite) and the like.

Note that, where interferon γ, TGF-β and a cytokine such as interleukin-4 or interleukin-13 are produced but any one of them is not dominantly produced, this is not preferable in view of the effect of the invention.

The antibody production-inducing agent of the present invention can be used as a pharmaceutical composition for preventing or treating diseases as mentioned above, such as allergic diseases, proliferative diseases such as cancers, bone diseases, age-related macular degeneration, multiple sclerosis, psoriasis vulgaris, and infections. Thus, according to the present invention, pharmaceutical compositions comprising the aforementioned antibody production-inducing agent are also provided.

Accordingly, the present invention further provides a method for preventing or treating a disease as mentioned above, comprising administering the aforementioned MAP or the aforementioned antibody production-inducing agent to a subject. In this method, the production of an antibody is the production of a class-switched antibody without being mediated by T cells, particularly including production of IgG antibody, IgA antibody or IgE antibody without being mediated by T cells, and preferably production of IgG antibody. Since the peptide to be bound to the MAP can be freely set without being restricted by known B cell epitope sequences, the antibody desired by a subject can be theoretically induced in the body. An antibody can be produced by the method of the present invention for the purpose of treating or preventing a disease.

Examples of an administration route include, but are not limited to, intravenous administration, transmucosal administration, intrarectal administration, subcutaneous administration, intramuscular administration, and oral administration routes.

The present invention further provides a method for preparing an antibody of interest. The method comprises a step (a) of administering the MAP of the present invention to a subject. This method may further comprise a step (b) of obtaining from a subject a biological sample containing B cells producing an antibody that binds to a B-cell recognition peptide contained in the MAP; a step (c) of selecting B cells from the biological sample collected in the step (b); and a step (d) of collecting the antibody by culturing the B cells.

The present invention further provides a method for screening for an antibody that binds to a B-cell recognition peptide contained in the MAP of the present invention from a biological sample obtained from a subject to which the MAP is administered. According to another aspect, the present invention comprises a method for collecting an antibody that binds to a B-cell recognition peptide contained in the MAP of the invention from a biological sample obtained from a subject to which the MAP is administered. These methods can be used to evaluate that an antibody is produced in a subject to which the MAP of the invention is administered.

According to another aspect, the present invention is also applicable to preparation of monoclonal antibodies. In a conventional technique, a monoclonal antibody is prepared by: immunizing an experimental animal (for example, mouse) with an antigen; removing spleen cells from the animal when both of T cells and B cells are sufficiently reacted; fusing the spleen cells with a hybridoma; and screening for fused cells successfully producing an antibody. Unless T cells and B cells are sufficiently reacted, it is difficult to obtain an intended monoclonal antibody. However, in the present invention, it is possible to produce an antibody without being mediated by T cells. It becomes easy to obtain an antibody that recognizes an intended antigen by activating B cells alone while ignoring T cells.

Furthermore, according to the present invention, since an antibody recognition region can be freely designed by peptide sequences, an antibody recognizing an intended region can be obtained, whereas the recognition region of a monoclonal antibody prepared by the conventional method depends upon recognition of T cells and B cells in the body of an immunized animal. As such, the present invention facilitates not only to develop a therapeutic drug or a prophylactic drug but also to obtain a monoclonal antibody required for research.

Furthermore, it is possible to specify gene sequences encoding antigen recognition regions (specifically, parts containing complementarity determining regions (CDRs)) of heavy and light chains of an antibody, or amino acid sequences of the antigen recognition regions of an antibody, by using the antibody-producing B cells that produce the monoclonal antibody. Based on the sequence information, recombinant antibodies such as a human antibody, a humanized antibody and a single-chain antibody can be generated by using gene recombination technology.

EXAMPLES

The present invention will be more specifically described referring to Examples; however, the scope of the invention is not limited by Examples.

Example 1

<Peptide Sequence>

Of the amino acid sequences of CH3 regions of human, dog and mouse IgE antibodies, the sequence of a site that has a high homology and protrudes outside in the three dimensional structure of the protein (aa293-304) was employed as a synthetic peptide in experiments below. Particularly, in the case where IgE already bound to mast cells was present, the peptide in a MAP had to be designed so as not to induce degranulation of the mast cells by crosslinking the IgE with the anti-IgE antibody induced by the MAP. Because of this, in the present invention, the peptide was designed by focusing the peptide that is a portion binding the IgE receptor. The sequences of the synthetic peptides are shown in Table 1. Note that the sequence actually used in the experiments below is the human sequence. Incidentally, when the human sequence is compared to the dog sequence and the mouse sequence, they differ in the amino acids underlined. When the human sequence is administered to a mouse, the amino acid portion underlined is recognized as a foreign substance by the mouse; whereas the other portions are recognized as the self in the mouse. Note that the 303rd and 304th amino acids (T and H) are a recognition site of the anti-IgE humanized antibody drug Omalizumab.

TABLE 1

| | | |
|---|---|---|
| Human sequence (the synthesized peptide sequence) | DWIEGETYQCRVTH | SEQ ID NO: 1 |
| Dog sequence (where a single amino acid differs from the above peptide) | DWIEGETY<u>Y</u>CRVTH | SEQ ID NO: 2 |
| Mouse sequence (where four amino acids differ from the above peptide) | DWIEG<u>YG</u>YQC<u>I</u>V<u>D</u>H | SEQ ID NO 3 |

The MAP core structure used herein is as follows.

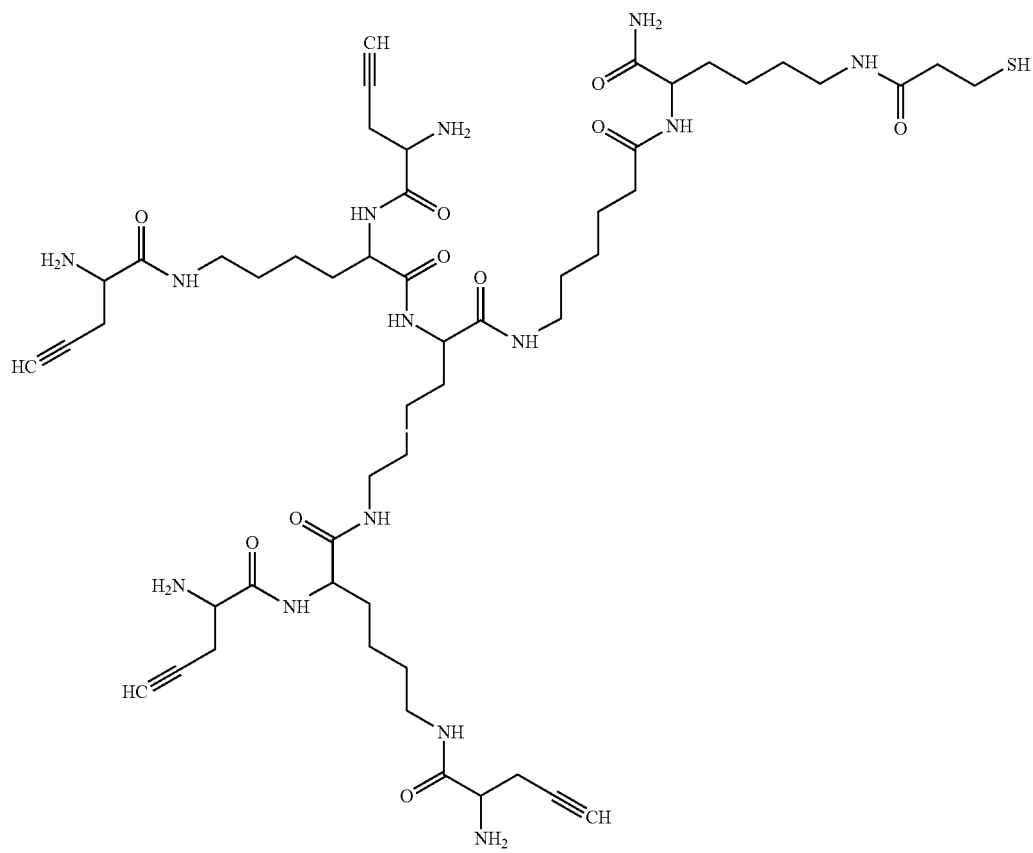 [SMILES: C#CCC(N)C(=O)NCCCCC(NC(=O)C(N)CC#C)C(=O)NCCCCC(NC(=O)C(CCCCNC(=O)C(N)CC#C)NC(=O)C(N)CC#C)C(=O)NCCCCCC(=O)NC(CCCCNC(=O)CCS)C(N)=O]

Four types of MAPs (i.e., MAP-2, MAP-4, MAP-8, and MAP-16) shown in FIG. 1 were synthesized by binding the peptide of the human sequence to the MAP core structure above.

Example 2

<Syntheses of B-Cell Recognition Peptide and MAP Core Peptide>

The B-cell recognition peptide and the MAP core peptide are synthesized by the method specifically described below.

The B-cell recognition peptide and the MAP core peptide were synthesized by the Fmoc solid-phase synthesis method. Specifically, using Fmoc-His(Trt)-TrtA-PEG Resin (0.1 mmol) as a solid-phase carrier, these peptides were synthesized in accordance with the steps shown in Table 2. The sequence of the B-cell recognition peptide was $N_3$-PEG-DWIEGETYQCRVTH-OH that was extended from the C-terminus towards N-terminus.

TABLE 2

| Step | Amino acid (mmol) | Reaction time (minutes) | Times |
|---|---|---|---|
| 1. Deblock | — | 7 | 1 |
| 2. Fmoc-amino acid | 0.4 | 15 | 1 |
| 3. Step 1 and Step 2, where the amino acid(s) was/were changed in accordance with the sequence, are repeated | | | |
| 4. Deblock | — | 7 | 1 |
| 5. $N_3$-PEG-COOH | 0.4 | 15 | 1 |

* After a step was completed, solid phase was sufficiently washed with DMF and then moved to the next step
* Upon reaction, the mixture was gently stirred using a reciprocating shaker
* Deblock refers to a step of deprotecting the N-terminal Fmoc group with a 20% piperidine/DMF solution
* Fmoc-amino acids used herein are as follows: Fmoc-Thr(tBu)-OH•Fmoc-Val-OH•Fmoc-Tyr(tBu)-OH•Fmoc-Gln(Trt)-OH•Fmoc-Cys(Trt)-OH•Fmoc-Arg(Pbf)-OH•Fmoc-Glu(OtBu)-OH•Fmoc-Gly-OH•-Fmoc-Ile-OH•Fmoc-Trp(Boc)-OH•Fmoc-Asp(OtBu)-OH
* The amino acids were coupled with each other in the following composition ratio (molar ratio).
Protected amino acid (mmol):HATU (mmol):DIEA (mmol):DMF (ml) = 0.4:0.4:0.8:2 ml After completion of the synthesis, thioanisole, m-cresol, TIPS and TFA were added in a ratio of 1.8:0.5:0.3:13 (ml) relative to the solid phase 0.1 mmol. The mixture was stirred for 1.5 hours, and then subjected to cut-out and de-protection. After the cut-out, the solution was recovered by filtration and concentrated under reduced pressure. To the resultant solution was ether added to recover a precipitate, thereby obtaining an unpurified peptide, which was then purified by reverse phase HPLC using 0.1% TFA and acetonitrile (ACN) as an eluate. The purified product was identified by mass spectrometry using MALDI-TOF MASS and whether a reaction product was obtained or not was determined.

Example 3

<Synthesis of MAP>

The MAP core peptide and the B-cell recognition peptide were bound through the Huisgen reaction. Specifically, alkynes of the MAP core were activated with Cu (I), and then allowed to react with the azido group at the N-terminus of the B-cell recognition peptide, whereby the peptide was bound to MAP core peptide via triazole formed.

As an example, specific synthesis steps of MAP 4 will be described below.

(Step 1)

A MAP core peptide and a B-cell recognition peptide are dissolved in an 8M aqueous urea solution. Specifically, the MAP core peptide 1 mg (0.9 µmol) and the B-cell recognition peptide 14 mg (7.2 µmol) are mixed in its mixing ratio and dissolved in an 8M aqueous urea solution 1.8 ml. This solution is called "peptide solution."

(Step 2)

An aqueous solution of copper sulfate pentahydrate and an aqueous solution of ascorbic acid are prepared.

The aqueous solution of copper sulfate pentahydrate is prepared by dissolving copper sulfate pentahydrate 18 mg (72 µmol) in 0.5 ml of distilled water (D. W.). This solution is called "aqueous copper sulfate solution."

The aqueous solution of ascorbic acid is prepared by dissolving ascorbic acid 63 mg (358 µmol) in 0.5 ml of D. W. This solution is called "aqueous ascorbic acid solution."

The aqueous copper sulfate solution 0.2 ml and the aqueous ascorbic acid solution 0.2 ml are mixed. This solution mixture is called "$Cu^+$ solution."

(Step 3)

The MAP core peptide and the B-cell recognition peptide are bound by the Huisgen reaction.

The Huisgen reaction is a reaction for binding an alkyne and an azide in the presence of a monovalent copper ion as the catalyst. The reaction product is stable and substantially free from a side reaction. This reaction attracts attention as click chemistry. The Huisgen reaction will be outlined below.

The $Cu^+$ solution was prepared by using the aqueous copper sulfate pentahydrate solution and ascorbic acid as in the step 2 and used in the following Huisgen reaction.

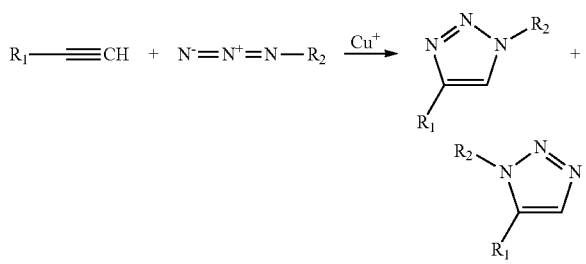

The mixing ratio (molar ratio) of components in the entire reaction system is as follows: MAP core:B-cell recognition peptide:copper sulfate pentahydrate:ascorbic acid=1:8:8:40.

The peptide solution 1.8 ml and the $Cu^+$ solution 0.2 ml were mixed and allowed to react at room temperature from a few hours to overnight. The reaction product was purified by reverse phase HPLC using an eluate containing 0.1% TFA and ACN and lyophilized.

The reaction product was identified by mass spectrometry using MALDI-TOF MASS.

Example 4

Experiment 1 Administering to Mouse: Determination of the Number of Peptides Bound to MAP The experiment was carried out in order to select a MAP having a high antibody inducing ability from MAP-2, MAP-4, MAP-8 and MAP-16. Balb/c mice (female, 6 week-old) were grouped as shown in Table 3, and MAPs or physiological saline (negative control) was administered to the mice.

TABLE 3

| Group | Administered agent | Administration concentration | Dosage | Number of mice |
|---|---|---|---|---|
| 1 | MAP-2 | 10 µg/100 µL | 100 µL IV | 6 |
| 2 | MAP-4 | 10 µg/100 µL | 100 µL IV | 6 |
| 3 | MAP-8 | 10 µg/100 µL | 100 µL IV | 6 |
| 4 | MAP-16 | 10 µg/100 µL | 100 µL IV | 6 |
| 5 (negative control) | Physiological saline | 0 µg/100 µL | 100 µL IV | 3 |

Figure 2:
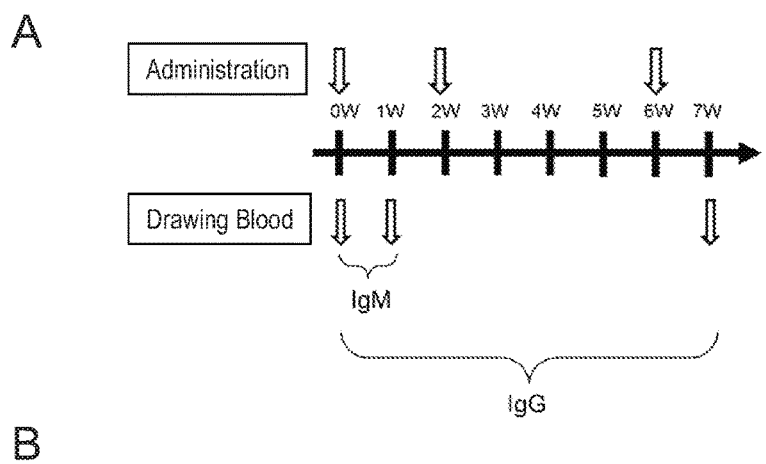
FIG. 2 This figure shows an administration/blood drawing schedule (A) for intravenous administration of each MAP (Group 1 to Group 4) or physiological saline (negative control, Group 5) to Balb/c mice (female, 6 week-old) without an adjuvant and for evaluation of an antibody inducing ability, wherein the schedule was carried out in order to select a MAP having a high antibody inducing ability from among MAP-2, MAP-4, MAP-8 and MAP-16, and shows the measurement results of IgM antibody titer (left of B) and IgG antibody titer (right of B) in individual groups.
Figure 2:
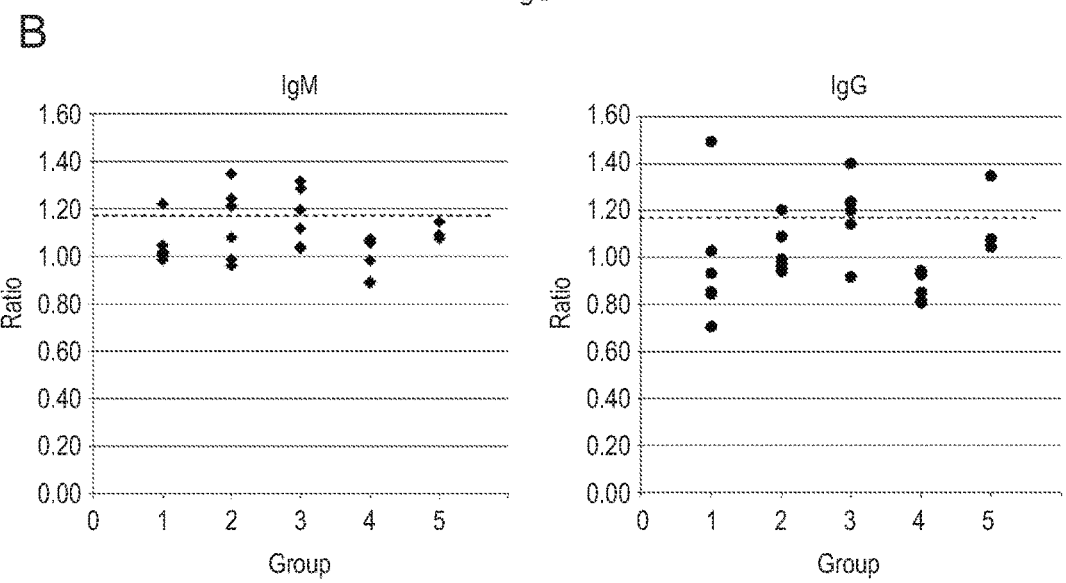

According to the schedule shown in FIG. 2A, the experiment was conducted over 7 weeks (0 W to 7 W, where W represents week). During this period, each MAP was administered to the mice three times (administration time points: 0 W, 2 W and 6 W) and blood was drawn from the mice three times (blood collection time points: 0 W, 1 W and 7 W).

The antibody titer was measured by ELISA using dog IgE immobilized onto a solid phase. Specifically, dog IgE (Bethyl Laboratories) was immobilized onto the solid phase of an ELISA plate at a concentrate of 0.1 µg/ml, at 4° C. overnight. The mouse serum was diluted 500 fold with a blocking buffer, added and reacted. Thereafter, the plate was washed and a 5000-fold diluted biotin-labeled anti-mouse IgG donkey antibody (Rockland) was used for detection of mouse IgG, and a 5000-fold diluted biotin-labeled anti-mouse IgM goat antibody (Rockland) was used for detection of mouse IgM. In addition, streptavidin-bound β-galactosidase was added and then 4-Methyl Umberlliferyl β-D-Galactoside (4MU) was added as a fluorescent substrate. Finally, fluorescence intensity was measured using a fluorescence plate reader. The IgM value in each mouse was indicated by the ratio of the value of 1 W relative to the value of 0 W, and the IgG value was indicated by the ratio of the value of 7 W relative to the value of 0 W.

The results are shown in FIG. 2B. In Group 2 (MAP-4) and Group 3 (MAP-8), it was found that both IgM and IgG tended to increase compared to other Groups. Accordingly, it was demonstrated that MAP-4 and MAP-8 had an expected antibody production effect. In Group 4 (MAP-16), neither IgM nor IgG increased. In addition, it was further found that immune reaction or antibody production did not occur in MAP-16.

Example 5

Experiment 2 Administering to Mouse: Determination of Optimal Dosages of MAP-4 and MAP-8

Subsequently, optimal dosages for antibody induction were examined by varying the dosages of MAP-4 and MAP-8. In the experiment, Balb/c mice (female, 6 week-old) were used. The mice were grouped as shown in Table 4. A single dose of each of these MAPs was determined in the range of 0.001 µg to 1 µg per mouse. MAP-4 was administered to Groups 1 to 4; MAP-8 was administered to Groups 5 to 8; and physiological saline was administered to Group 9 and used as a negative control.

TABLE 4

| Group | Administered agent | Administration concentration | Dosage | Number of mice |
|---|---|---|---|---|
| 1 | MAP-4 | 1 µg/100 µL | 100 µL IV | 3 |
| 2 | MAP-4 | 0.1 µg/100 µL | 100 µL IV | 3 |
| 3 | MAP-4 | 0.01 µg/100 µL | 100 µL IV | 4 |
| 4 | MAP-4 | 0.001 µg/100 µL | 100 µL IV | 3 |
| 5 | MAP-8 | 1 µg/100 µL | 100 µL IV | 4 |
| 6 | MAP-8 | 0.1 µg/100 µL | 100 µL IV | 4 |
| 7 | MAP-8 | 0.01 µg/100 µL | 100 µL IV | 4 |
| 8 | MAP-8 | 0.001 µg/100 µL | 100 µL IV | 4 |
| 9 (negative control) | Physiological saline | 0 µg/100 µL | 100 µL IV | 2 |

Figure 3:
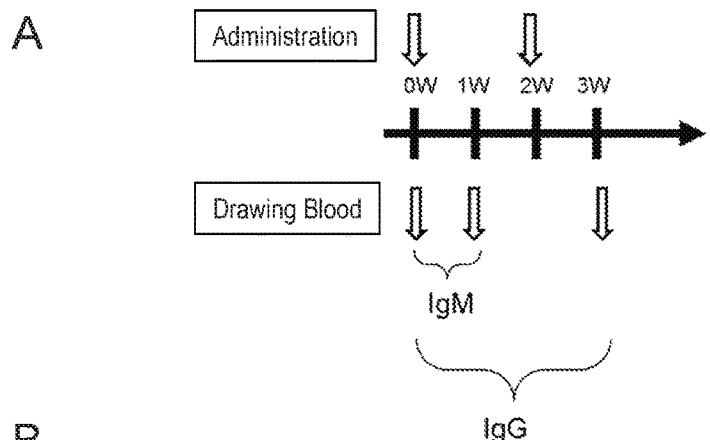
FIG. 3 This figure shows an administration/blood drawing schedule (A) for administration of MAP-4 (Group 1 to Group 4), MAP-8 (Group 5 to Group 8) or physiological saline (negative control, Group 9) to Balb/c mice (female, 6 week-old), wherein the schedule was carried out in order to determine optimal dosages for inducing antibodies by varying the dosages of MAP-4 and MAP-8, and shows the measurement results of antibody titer of IgM (upper left and upper right of B) and the pre-ratio of IgG (lower left and lower right of B) relative to mouse IgE (Ms IgE) and dog IgE (Dog IgE) in individual groups.
Figure 3:
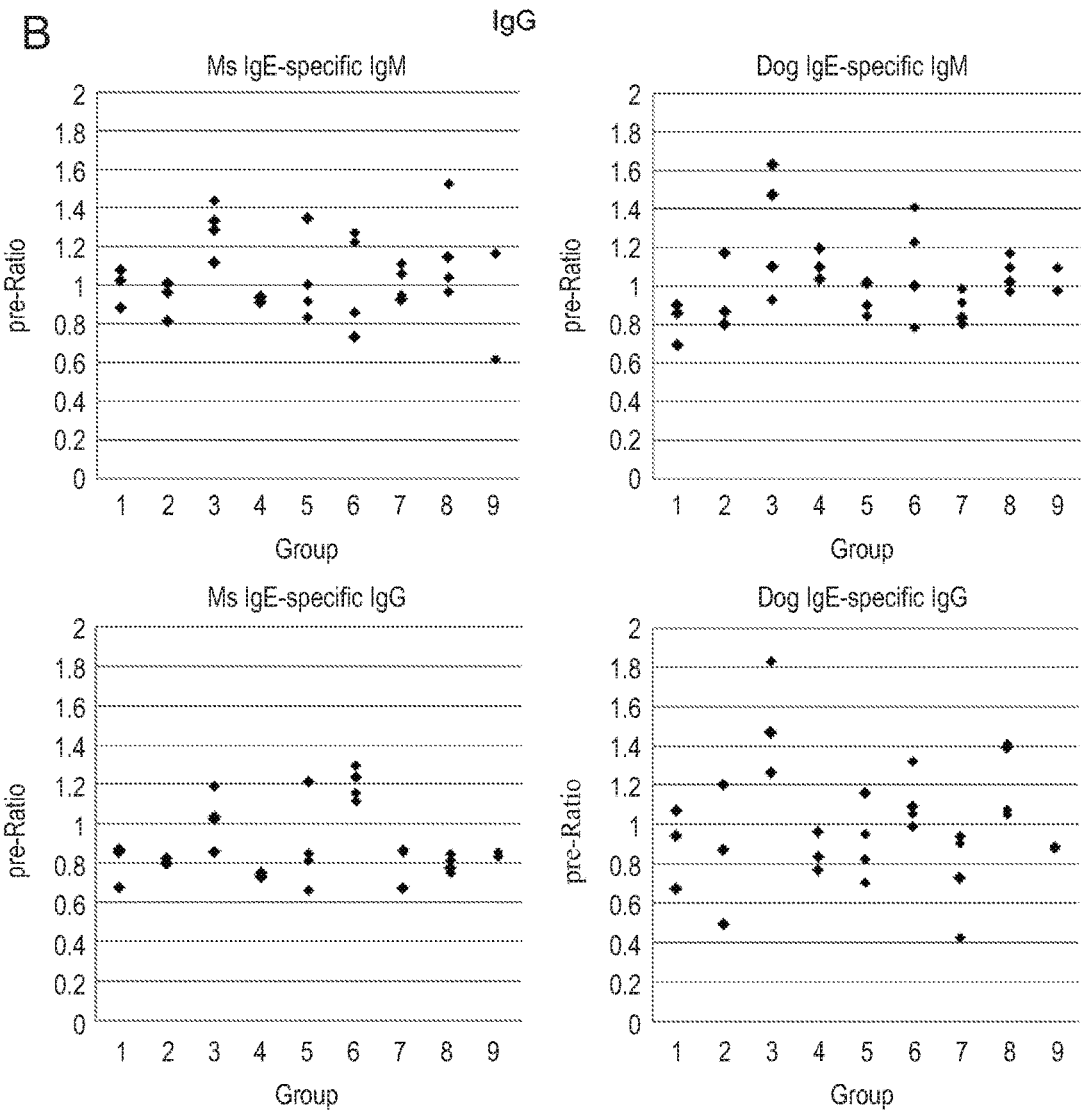

The administration schedule is as shown in FIG. 3A. The agents were administered to the mice at week 0 (0 W) and at week 2 (2 W), and blood was drawn from the mice at 0 W, 1 W and 3 W. IgM and IgG were measured as described above. The value at 1 W was compared to the value at 0 W (IgM measurement), and the value at 3 W was compared to the value at 0 W (IgG measurement). In the experiment, the antibody titers relative to not only dog IgE but also mouse IgE were measured.

The results are shown in FIG. 3B. It was considered that the dosage of Group 3 in MAP-4 administration groups was optimal (dosage: 0.01 µg/administration); and that the dosage of Group 6 in MAP-8 administration groups was the most optimal for antibody induction (dosage: 0.1 µg/administration). In addition, it was found that the optimal dosage differs between MAP-4 and MAP-8.

Example 6

Experiment 3 Administrating to Nude Mouse: Demonstration of the Idea that IgG is Induced by MAP Alone It was so far known that, while IgM is induced by an antigen which is not mediated by T cells, any class-switching to IgG does not occur. This is because it is necessary for antibody-producing B cells to receive interferon γ stimulation from T cells in order to class-switch to IgG, and, to do so, it is necessary to exchange antigen information, or to recognize T cell epitopes, between T cells and B cells. In other words, for IgG production by a MAP, T cell-mediated antigen-specific reaction is essential. As such, to cause T cell-mediated reaction using a MAP, a combination T cell epitope and B cell epitope was inserted into the peptide portion of the MAP, according to the so far obtained findings (Non-Patent Literature 1 and Non-Patent Literature 2). In addition, to force T cells to recognize the epitope, an adjuvant having such action has concomitantly been administered.

In contrast, production of IgG by MAP, e.g. MAP-4 or MAP-8, according to the present invention is caused by administration of a B cell epitope alone to which the present inventors wish to induce an antibody without mediating T cells. Then, the present inventors predicted that IgG might be produced by B cells stimulated by MAP-4 or MAP-8 that was stimulated by nonspecific (which means is independent on a T cell epitope) interferon γ, and carried out the following experiments.

Figure 4:
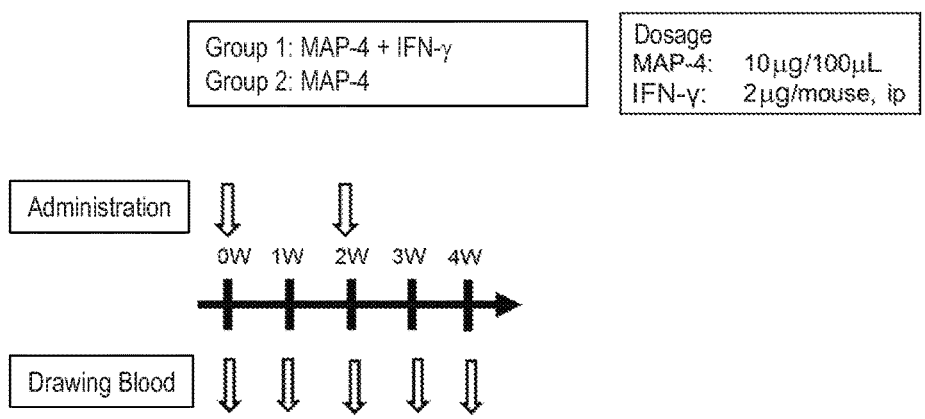
FIG. 4 shows administration/blood drawing schedule (A) of the case (Group 1) where MAP-4 and a mouse interferon-γ preparation (PeproTech) were concomitantly administered to T-cell defective mice (nude mice, 8 week-old, female) and the case (Group 2) where MAP-4 alone was administered: and the measurement results (B) of the amount of IgG relative to that of dog IgE with respect to Group 1 (left) and Group 2 (right). In Group 1, ■ represents mouse 1, x mouse 2, ▲ mouse 3, * mouse 4 and ♦ mouse 5. In Group 2, ■ represents mouse 6, x mouse 7, ▲ mouse 8 and ♦ mouse 9.
Figure 4:
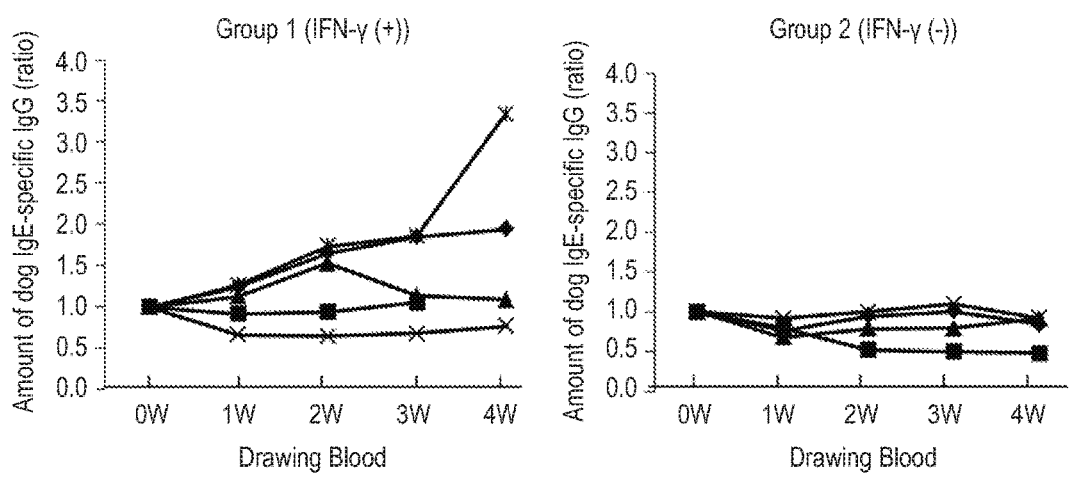

In order to verify the aforementioned concept, the present inventors conducted administration experiments of MAP-4 using T cell deficient mice (nude mice). To nude mice (8 week-old, female), MAP-4 and a mouse interferon γ preparation (PeproTech) were concomitantly administered as shown in FIG. 4A. IgG production was examined between the concomitant administration group and a group administered only with MAP-4 without administration of the interferon γ preparation. The interferon γ preparation was intravenously administered three times at 6-hour intervals on the same day as MAP-4 administration. Every one week before and after the administration up to 4 weeks, blood was drawn from each mouse in order to examine changes of IgM and IgG antibody titers with time.

As a result, as shown in the graph of FIG. 4B, in a group (Group 1) to which interferon γ was administered, the IgG antibody titer relative to anti-dog IgE rised in 3 out of 5 mice, whereas IgG antibody titer did not rise in all mice in a group (Group 2) not administered with interferon γ.

From the results, it was found that B cells stimulated with MAP-4 or MAP-8 produce IgG upon stimulation with nonspecific interferon γ observed in MAP administration, as predicted by the present inventors.

To verify that IgG to dog IgE in Group 1 in the above experiment was the same as IgG to mouse IgE (which is really an autoantibody to mouse IgE), the inventors subsequently measured IgG antibody titer to mouse IgE; and simultaneously conducted inhibition tests by previously adding dog IgE in the serum. In this experiment, the serum exhibiting the highest antibody titer in the above nude mouse experiment was used.

Specifically, the antibody titer of mouse IgG was measured by ELISA using mouse IgE immobilized onto a solid phase. On the other hand, dog IgE (Bethyl Laboratories) was previously added to the same serum and allowed to react and thereafter, mouse IgG to mouse IgE was measured.

Figure 5:
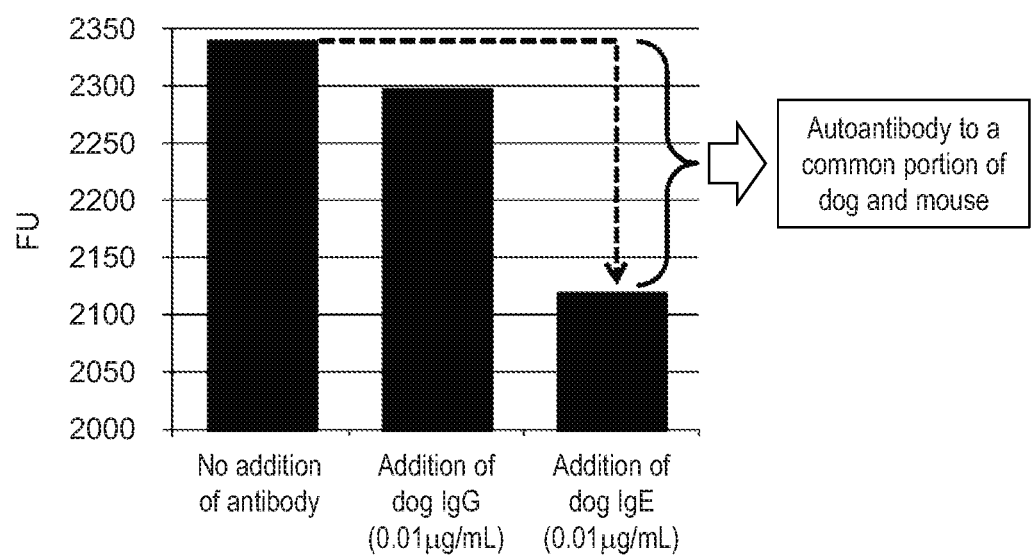
FIG. 5 This figure is a graph showing that an autoantibody to IgE is induced by MAP-4 in the bodies of mice.

The results are shown in FIG. 5. From the figure, it was observed that IgG to mouse IgE increased and, at the same time, the measured values decreased in the serum to which dog IgE was previously added. In the measurement of the control sample where dog IgG (Bethyl Laboratories) was added to the serum, the decrease was extremely low. Accordingly, it was found that the portion inhibited with dog IgE was an antibody recognizing both dog IgE and mouse IgE, thus demonstrating that an autoantibody to mouse IgE was induced by MAP-4 in the body of the mouse.

As mentioned above, it was demonstrated through the above-described experiments that the MAP induced an autoantibody to IgE. This means that an intended IgG can be produced only by a chemical compound having the MAP structure without being mediated by T cells; and that IgG can be induced by a foreign antigen except an autoantibody. Furthermore, in the present invention, the number of peptides in MAP, effective for inducing IgG can be determined 4 to 8.

Example 7

<Change of *Dermatophagoides farinae*-Specific IgE in Sensitized Dog>

Figure 6:
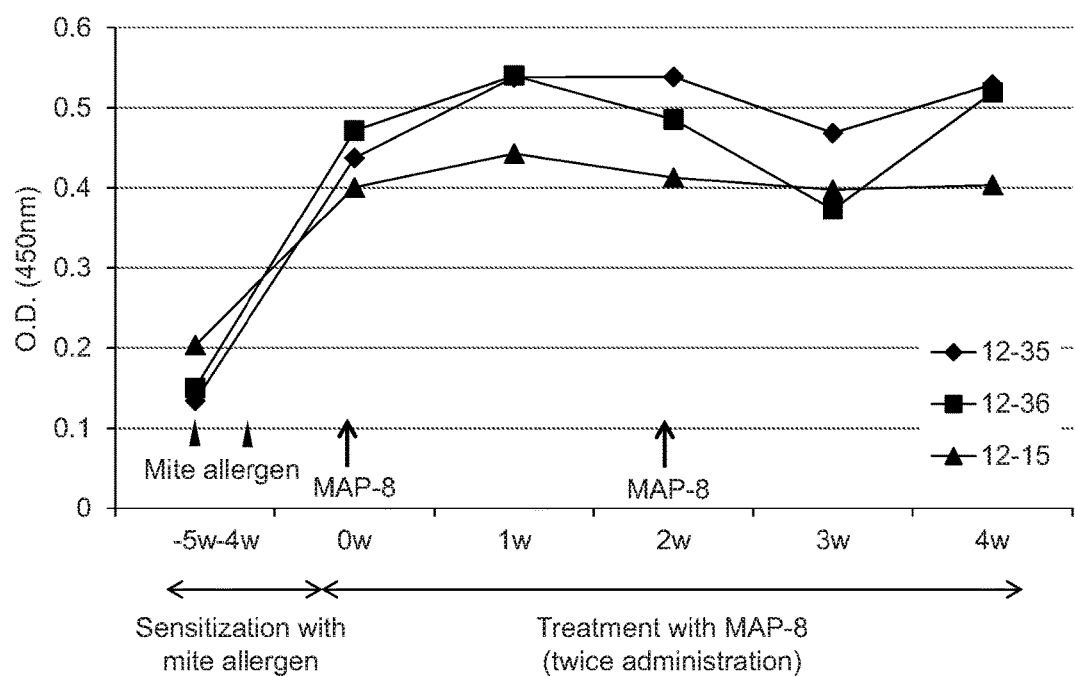
FIG. 6 This figure shows a time-dependent change (O.D.450 nm) of *Farinae* specific IgE when MAP-8 was intravenously administered concomitantly with Alum adjuvant to dogs sensitized with a *Farinae* antigen (allergen). In this figure, the dogs treated are 12-35 (♦) and 12-36 (■), and the dog that is a negative control administered with physiological saline is 12-15 (▲).

Three beagle dogs were each subcutaneously administered with 250 µg of *Dermatophagoides farinae* antigen (Greer Laboratories, Inc.) and 25 mg of Alum (Aluminum hydroxide) adjuvant, twice at an interval of a week. After an increase of *Dermatophagoides farinae*-specific IgE was observed (0 w), two dogs (12-35 and 12-36) to be treated were intravenously injected with 1 mL of physiological saline containing 500 μg of MAP-8 (the same as in Example 5). The other dog (12-15) to be used as a negative control was intravenously injected with 1 mL of physiological saline. At the first week after second administration of MAP-8, by which anti-IgE autoantibody was regarded as being produced by the MAP administration, *Dermalophagoides farinae*-IgE decreased. In contrast, *Dermatophagoides farinae*-IgE of the negative-control dog did not decrease. The results are shown in FIG. 6. Note that since the IgE level in blood is controlled so as to be constant in the body of the mouse, the level of IgE increased in the next week even in the dogs treated. In this case, it is expected that the therapeutic effect can be increased by a plurality of MAP-8 administrations or by increasing (or enhancing) production of interferon γ simultaneously with MAP-8 administration.

Example 8

<Examination of Effect of Suppressing an Increase of IgE in a Boost State with an Allergen>

Figure 7:
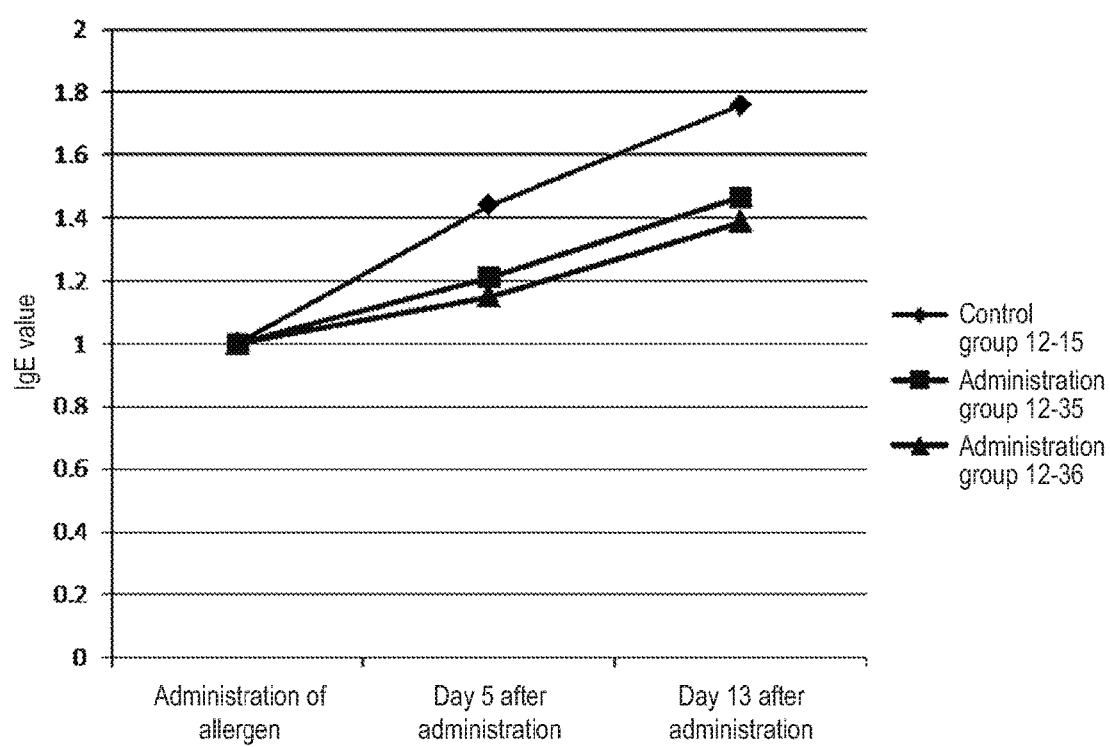
FIG. 7 This figure shows a *Dermatophagoides farinae*-IgE value ratio after MAP-8 was intravenously administered, and then *Dermatophagoides farinae* antigen (allergen boost) with Alum adjuvant was administered subcutaneously, concomitantly with Alum adjuvant to a dog sensitized with a *Dermatophagoides farinae* antigen (allergen), where the IgE value at the time point of allergen boost administration is represented as 1.0. The dogs treated are 12-35 (■) and 12-36 (▲), and the dog that is a negative control administered with physiological saline is 12-15 (♦).

Three beagle dogs (one year-old, two female dogs, one male dog) were each subcutaneously injected twice with 250 μg of a crude *Dermatophagoides farinae* antigen (manufactured by Greer) and 25 mg of Alum adjuvant. In this manner, the dogs were sensitized with the allergen. After a sufficient increase of IgE against *Dermatophagoides farinae* was confirmed, MAP-8 dissolved in 1 ml physiological saline was intravenously injected three times at intervals of two weeks at a dosage of 500 μg/dog/time (where two dogs 12-35 and 12-36 were administration groups). The other dog as a control group was injected with the same amount of physiological saline. Thereafter, an IgE value against *Dermatophagoides farinae* was measured at regular intervals but no change was observed. Thus, after 8 weeks, the dogs were subcutaneously injected with a crude antigen of *Dermatophagoides farinae* (100 μg) to boost allergen (indicated by the allergen administration in the graph). On day 4 after the allergen administration, the same amount of MAP-8 was intravenously injected. The IgE value against *Dermatophagoides farinae* was measured on day 5 and day 13 after the allergen administration. An increase ratio of IgE against *Dermatophagoides farinae* to the measurement value at the time of the "allergen administration" regarded as 1.0 was calculated. As a result, the increase of IgE value against *Dermatophagoides farinae* of the administration group compared to the control group was weak. From this, it was found that an IgE increase was suppressed by administration of MAP-8 during exposure to allergen. The results are shown in FIG. 7.

INDUSTRIAL APPLICABILITY

The present invention provides a multiplexed same type-antigenic peptide having 4 to 8 B-cell recognition peptides. The multiplexed same type-antigenic peptide of the present invention enables to produce a class-switched antibody in vivo without being mediated by T cells, even if an adjuvant is not used. Thus, it was demonstrated that an antibody to a substance against which an antibody has been rarely induced could be prepared according to the present invention.

For example, as long as a multiplexed same type-antigenic peptide has a B-cell recognition peptide derived from a peptide contained in a predetermined protein involved in a disease, the multiplexed same type-antigenic peptide can be used in place of an antibody drug. The present invention can also be used as a vaccine against an infection against which a vaccine has not been able to successfully produce in the art, and against a newly emerged infection.

As described above, since the present invention makes it possible to easily prepare an autoantibody whose production has been considered to be impossible and an antibody to a foreign antigen, the invention has extremely high industrial usefulness.

All publications, patents and patent applications cited therein are incorporated herein in their entirety by reference.

The invention claimed is:

1. A multiplexed same type-antigenic peptide comprising a dendritic core and B-cell recognition peptides, wherein the multiplexed same type-antigenic peptide comprises 4 to 8 B-cell recognition peptides of the same type, which are bound to the terminal ends of the dendritic core directly or via a spacer, and production of a class-switched antibody is induced by directly stimulating B cells in vivo in the absence of a T cell epitope; wherein the dendritic core has the following structure:

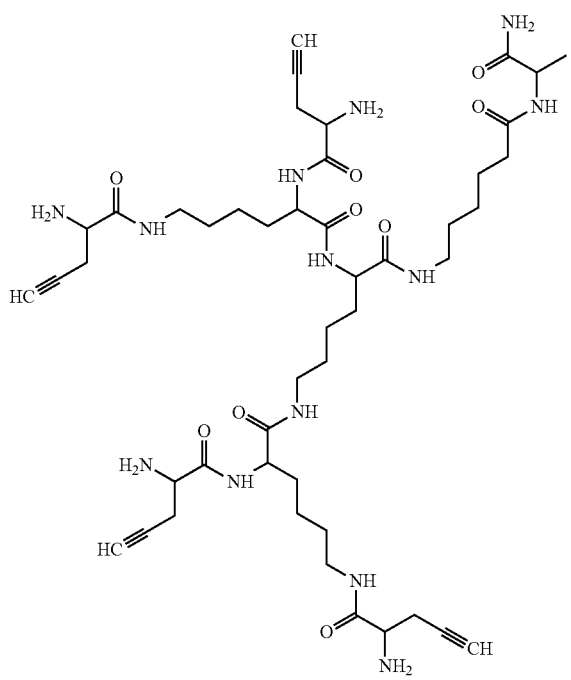

-continued

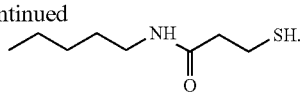

2. The multiplexed same type-antigenic peptide according to claim 1, wherein the B-cell recognition peptide is a peptide consisting of 7 to 50 amino acid residues.

3. The multiplexed same type-antigenic peptide according to claim 1, wherein the B-cell recognition peptide is an autoantigen.

4. The multiplexed same type-antigenic peptide according to claim 3, wherein the autoantigen is an antigen from IgE.

5. An antibody production-inducing agent comprising the multiplexed same type-antigenic peptide according to claim 1, as an active ingredient.

6. The antibody production-inducing agent according to claim 4, further comprising interferon γ and/or an adjuvant having an ability to produce interferon γ.

7. The antibody production-inducing agent according to claim 4, wherein the antibody is an IgG antibody.

8. The antibody production-inducing agent according to claim 4, wherein the antibody production-inducing agent is a vaccine.

9. A pharmaceutical composition comprising the antibody production-inducing agent according to claim 4.

10. A method for producing the multiplexed same type-antigenic peptide according to claim 1, comprising:
   (a) providing a dendritic core having reactive functional groups;
   (b) providing a plurality of B-cell recognition peptides of the same type having reactive functional groups;
   (c) effecting a binding reaction of the reactive functional group of the dendritic core with the reactive functional group of each B-cell recognition peptide to prepare the multiplexed antigenic peptide; and
   (d) collecting the multiplexed antigenic peptide.

* * * * *